United States Patent
Aharon et al.

(10) Patent No.: US 8,617,281 B2
(45) Date of Patent: Dec. 31, 2013

(54) METHODS AND SYSTEMS FOR FEEDSTOCK PRODUCTION FROM SEWAGE AND PRODUCT MANUFACTURING THEREFROM

(75) Inventors: Refael Aharon, Maalle (IL); Israel Biran, Avihail (IL); Ronny Banker, Ramat-Gan (IL)

(73) Assignee: Applied Cleantech, Inc, Newton, MA (US)

( * ) Notice: Subject to any disclaimer, the term of this patent is extended or adjusted under 35 U.S.C. 154(b) by 449 days.

(21) Appl. No.: 12/700,976

(22) Filed: Feb. 5, 2010

(65) Prior Publication Data

US 2010/0196981 A1 Aug. 5, 2010

Related U.S. Application Data

(63) Continuation-in-part of application No. PCT/US2008/009679, filed on Aug. 13, 2008, and a continuation-in-part of application No. PCT/US2009/033802, filed on Feb. 11, 2009, which is a continuation-in-part of application No. PCT/US2008/009679.

(60) Provisional application No. 60/935,429, filed on Aug. 13, 2007, provisional application No. 61/071,842, filed on May 21, 2008, provisional application No. 61/088,350, filed on Aug. 13, 2008, provisional application No. 61/150,007, filed on Feb. 5, 2009, provisional application No. 61/185,594, filed on Jun. 10, 2009.

(51) Int. Cl.
*C05D 9/02* (2006.01)
*C05F 11/00* (2006.01)

(52) U.S. Cl.
USPC .......................................... 71/12; 71/11; 71/23

(58) Field of Classification Search
USPC ..................... 71/11, 23, 24; 127/37
See application file for complete search history.

(56) References Cited

U.S. PATENT DOCUMENTS

| 3,579,320 A | 5/1971 | Presses |
| 3,670,968 A | 6/1972 | Galeano |

(Continued)

FOREIGN PATENT DOCUMENTS

| CA | 2095979 | 9/1994 |
| DE | 4121104 A1 | 10/1992 |

(Continued)

OTHER PUBLICATIONS

Kataoka et al. JP 63315197A; Dec. 22, 1988 (Abstract Only).

(Continued)

*Primary Examiner* — Jennifer Smith

(74) *Attorney, Agent, or Firm* — Mintz Levin Cohn Ferris Glovsky and Popeo, P.C.; Ivor R. Elrifi; Matthew Pavao

(57) ABSTRACT

A cellulosic feedstock composition including an oil content of up to 15% of the composition, a cellulose content of 40-99% of the composition, a hemicellulose content of 2-20% of the composition, a lignin content of less than 15% of the composition, a nitrogen containing organic compound content of less than 20% of the composition, a protein containing organic compound content of less than 20% of the composition, a mineral content of less than 5% of the composition, a sand content of less than 5% of the composition, and a dirt content of less than 25% of the composition.

12 Claims, 23 Drawing Sheets

(56) References Cited

U.S. PATENT DOCUMENTS

| | | |
|---|---|---|
| 3,680,796 A | 8/1972 | Galeano |
| 3,711,392 A | 1/1973 | Metzger |
| 3,814,336 A | 6/1974 | Brewer |
| 3,849,246 A | 11/1974 | Raymond et al. |
| 3,897,301 A | 7/1975 | Bauman et al. |
| 3,909,397 A | 9/1975 | Aldinger |
| 3,911,808 A | 10/1975 | Lassiter et al. |
| 3,933,577 A | 1/1976 | Penque |
| 4,185,680 A | 1/1980 | Lawson |
| 4,219,381 A | 8/1980 | Schnell |
| 4,279,741 A | 7/1981 | Campbell |
| 4,405,450 A | 9/1983 | Selder |
| 4,427,541 A | 1/1984 | Crosby et al. |
| 4,440,635 A | 4/1984 | Reiniger |
| 4,486,459 A | 12/1984 | Thompson |
| 4,545,900 A | 10/1985 | Wright |
| 4,570,861 A | 2/1986 | Zentgraf et al. |
| 4,846,975 A | 7/1989 | Kelyman |
| 4,849,116 A | 7/1989 | Weinmann et al. |
| 4,874,134 A | 10/1989 | Wiens |
| 4,895,642 A | 1/1990 | Frei |
| 4,974,781 A | 12/1990 | Placzek |
| 5,024,335 A | 6/1991 | Lundell |
| 5,100,066 A | 3/1992 | Frei |
| 5,292,075 A | 3/1994 | Bartlett |
| 5,297,742 A | 3/1994 | Grunditz et al. |
| 5,571,703 A | 11/1996 | Chieffalo et al. |
| 6,048,458 A | 4/2000 | Vogt et al. |
| 6,207,015 B1 | 3/2001 | Templer et al. |
| 6,238,516 B1 | 5/2001 | Watson et al. |
| 6,244,446 B1 | 6/2001 | Schmittel |
| 6,250,472 B1 | 6/2001 | Grubbs et al. |
| 6,336,992 B1 | 1/2002 | Blomquist |
| 6,379,527 B1 | 4/2002 | Vogt et al. |
| 6,555,350 B2 * | 4/2003 | Ahring et al. ............ 435/162 |
| 2002/0060014 A1 | 5/2002 | Sipila et al. |
| 2002/0157989 A1 | 10/2002 | Gatlin et al. |
| 2003/0141225 A1 | 7/2003 | Liddle et al. |
| 2004/0035959 A1 | 2/2004 | Hautala |
| 2004/0209753 A1 | 10/2004 | Kikushima et al. |
| 2006/0101881 A1 * | 5/2006 | Carin et al. ............ 71/21 |
| 2007/0098625 A1 | 5/2007 | Adams et al. |
| 2007/0108406 A1 | 5/2007 | Schu |
| 2007/0175825 A1 | 8/2007 | Denney |
| 2009/0281302 A1 | 11/2009 | Aharon |

FOREIGN PATENT DOCUMENTS

| | | |
|---|---|---|
| DE | 10135678 A1 | 2/2003 |
| DE | 10150753 A1 | 7/2003 |
| EP | 0170301 A2 | 2/1986 |
| EP | 0658648 A2 | 6/1995 |
| EP | 0969076 A1 | 1/2000 |
| FR | 2780320 A1 | 12/1999 |
| GB | 264128 A | 5/1927 |
| GB | 275717 A | 8/1927 |
| GB | 444993 A | 4/1936 |
| GB | 457756 A | 12/1936 |
| GB | 601963 A | 5/1948 |
| GB | 704765 A | 3/1954 |
| GB | 741987 A | 12/1955 |
| GB | 748580 A | 5/1956 |
| GB | 912450 A | 12/1962 |
| GB | 985097 A | 3/1965 |
| GB | 1029001 A | 5/1966 |
| GB | 1416273 A | 12/1975 |
| GB | 1445698 A | 8/1976 |
| GB | 1477326 A | 6/1977 |
| GB | 1498706 A | 1/1978 |
| GB | 1502985 A | 3/1978 |
| GB | 1528236 A | 10/1978 |
| GB | 2172525 A | 9/1986 |
| JP | 63315197 A | 12/1988 |
| JP | 04-215811 | 8/1992 |
| JP | 04215811 A | 8/1992 |
| JP | 06-039368 | 2/1994 |
| JP | 06-269746 | 9/1994 |
| JP | 06267946 A | 9/1994 |
| JP | 11-116368 | 4/1999 |
| JP | 11-158789 | 6/1999 |
| JP | 2004283127 A | 10/2004 |
| WO | WO-9114504 A1 | 10/1991 |
| WO | WO-9612569 A1 | 5/1996 |
| WO | WO-9720643 A2 | 6/1997 |
| WO | WO-0072987 A1 | 12/2000 |
| WO | WO-0189730 A2 | 11/2001 |
| WO | WO-0234420 A2 | 5/2002 |
| WO | WO-2004003289 A1 | 1/2004 |
| WO | WO-2004/108609 A1 | 12/2004 |
| WO | WO-2005/113458 A1 | 12/2005 |
| WO | WO-2006095349 A1 | 9/2006 |
| WO | WO-2008/073186 A2 | 6/2008 |

OTHER PUBLICATIONS

Cheung, S.W. and Anderson, B.C. Laboratory Investigation of Ethanol Production from Municipal Primary Wastewater Solids. Bioresource Technology, 59:81-86. 1997.

* cited by examiner

RAW SEWAGE SOLID COMPOSITION VS. PULP/PAPER PRODUCT COMPOSITION

RAW SEWAGE COMPOSITION VS. GLUCOSE COMPOSITION

METHODS AND SYSTEMS FOR FEEDSTOCK PRODUCTION FROM SEWAGE AND PRODUCT MANUFACTURING THEREFROM

CROSS-REFERENCE TO RELATED APPLICATIONS

The present application is a continuation-in-part of PCT Application No. PCT/US2008/009679, filed on Aug. 13, 2008, which claims priority to, and the benefit of, U.S. Provisional Application No. 60/935,429, filed Aug. 13, 2007 and U.S. Provisional Application No. 61/071,842, filed May 21, 2008. The present application is also a continuation-in-part of PCT Application No. PCT/US2009/33802, filed on Feb. 11, 2009, which is a continuation-in-part of PCT Application No. PCT/US2008/009679, filed on Aug. 13, 2008. PCT Application No. PCT/US2009/33802 also claims priority to, and the benefit of, U.S. Provisional Application No. 61/071,842, filed May 21, 2008 and U.S. Provisional Application No. 61/088,350, filed Aug. 13, 2008. The present application also claims priority to, and the benefit of, U.S. Provisional Application No. 61/150,007, filed on Feb. 5, 2009 and U.S. Provisional Application No. 61/185,594, filed on Jun. 10, 2009. The contents of each of these applications is herein incorporated by reference in its entirety.

FIELD OF THE INVENTION

The present invention relates generally to methods and systems for producing feedstock from sewage and more specifically relates to methods and systems for producing cellulosic feedstock from sewage and manufacturing of products therefrom.

BACKGROUND OF THE INVENTION

Cellulose is an organic compound defined as a polysaccharide structured of a linear chain of several hundred to over ten thousand glucose units.

Fibers comprising cellulose can be found in sewage systems, such as municipal sewage waste systems, industrial waste systems and agricultural waste systems, for example.

The source of cellulose fibers in the municipal sewage waste system is typically from fruits and vegetables, paper, cloths and laundry refuse. For example, a cellulose fiber portion of raw sewage, i.e. untreated sewage, comprises generally 30-50% textile fibers, 10-35% vegetative fibers and 20-40% paper fibers.

SUMMARY OF THE INVENTION

There is thus provided in accordance with an embodiment of the present invention a cellulosic feedstock composition including an oil content of up to 15% of the composition, a cellulose content of 40-99% of the composition, a hemicellulose content of 2-20% of the composition, a lignin content of less than 15% of the composition, a nitrogen containing organic compound content of less than 20% of the composition, a protein containing organic compound content of less than 20% of the composition, a mineral content of less than 5% of the composition, a sand content of less than 5% of the composition, and a dirt content of less than 25% of the composition. Additionally, a caloric value of the composition is in the range of 5000-16000 BTU/Pounds. Moreover, the composition is produced from a solid portion of a sewage suspension, wherein the sewage suspension is included in a stream of sewage flowing in a Wastewater Treatment Plant (WWTP).

In accordance with an embodiment of the invention the composition is produced from the solid portion of the sewage suspension by removing the solid portion from the sewage suspension, removing sand from the solid portion, removing a mineral from the solid portion, and removing dirt from the solid portion, thereby producing the composition. Additionally, the composition is produced by any one of the following: at least partially drying the solid portion, dewatering the solid portion, and sterilizing the solid portion. Moreover, the composition is used to produce textile, a combustion product, a wood pellet, a wood chip, a fiberboard, plant media, pulp, paper, animal feed, animal media, glucose, a biofuel, butanol, propane butane or ethanol.

In accordance with another embodiment of the invention a combustion product composition produced from the cellulosic feedstock composition includes an oil content of 1-15% of the composition, a cellulose content of 40-90% of the composition, a hemicellulose content of 2-20% of the composition, a lignin content of less than 12% of the composition, a nitrogen containing organic compound content of less than 15% of the composition, a protein containing organic compound content of less than 15% of the composition, a mineral content of less than 5% of the composition, a sand content of less than 5% of the composition, and a dirt content of less than 5% of the composition. Additionally, a caloric value of the composition is in the range of 5000-16000 BTU/Pounds.

In accordance with yet another embodiment of the invention an ethanol containing composition produced from the cellulosic feedstock composition includes an oil content of 1-10% of the composition, a cellulose content of 50-90% of the composition, a hemicellulose content of 2-20% of the composition, a lignin content of less than 12% of the composition, a nitrogen containing organic compound content of less than 15% of the composition, a protein containing organic compound content of less than 15% of the composition, a mineral content of less than 5% of the composition, a sand content of less than 5% of the composition, and a dirt content of less than 5% of the composition. Additionally, a caloric value of the composition is in the range of 5000-16000 BTU/Pounds.

In accordance with yet another embodiment of the invention a pulp or paper product composition produced from the cellulosic feedstock composition includes an oil content of 1-10% of the composition, a cellulose content of 50-90% of the composition, a hemicellulose content of 2-20% of the composition, a lignin content of less than 4% of the composition, a nitrogen containing organic compound content of less than 15% of the composition, a protein containing organic compound content of less than 15% of the composition, a mineral content of less than 5% of the composition, a sand content of less than 5% of the composition, and a dirt content of less than 5% of the composition. Additionally, a particle size of the composition is in the range of 0.01 microns-100 mm.

In accordance with still another embodiment of the invention an animal feed or animal media composition produced from the cellulosic feedstock composition includes an oil content of 1-10% of the composition, a cellulose content of 50-90% of the composition, a hemicellulose content of 2-20% of the composition, a lignin content of less than 12% of the composition, a nitrogen containing organic compound content of less than 15% of the composition, a protein containing organic compound content of less than 15% of the composition, a mineral content of less than 5% of the composition, a sand content of less than 5% of the composition, and a dirt content of less than 5% of the composition. Additionally, a caloric value of the composition is in the range of 5000-16000 BTU/Pounds.

In accordance with still another embodiment of the invention a glucose containing composition produced from the cellulosic feedstock composition includes an oil content of 1-10% of the composition, a cellulose content of 50-90% of the composition, a hemicellulose content of 2-20% of the composition, a lignin content of less than 12% of the composition, a nitrogen containing organic compound content of less than 15% of the composition, a protein containing organic compound content of less than 15% of the composition, a mineral content of less than 5% of the composition, a sand content of less than 5% of the composition, and a dirt content of less than 5% of the composition.

There is thus provided in accordance with another embodiment of the present invention a method for producing a cellulosic feedstock composition from a solid portion of a sewage suspension including removing the solid portion from the sewage suspension, removing sand from the solid portion, removing a mineral from the solid portion, and removing dirt from the solid portion, thereby producing the cellulosic feedstock composition. Additionally, removing the solid portion includes removing the solid portion from a stream of sewage flowing in a WWTP, the sewage stream including the sewage suspension. Moreover, removing sand is operative to decrease a sand content of the composition to less than 5% of the composition. Furthermore, removing a mineral is operative to decrease a mineral content of the composition to less than 5% of the composition. Accordingly, removing dirt is operative to decrease a dirt content of the composition to less than 25% of the composition.

In accordance with an embodiment of the invention the method further includes at least one of the following: at least partially drying the solid portion, dewatering the solid portion, and sterilizing the solid portion. Accordingly, the composition includes an oil content of up to 15% of the composition, a cellulose content of 40-99% of the composition, a hemicellulose content of 2-20% of the composition, a lignin content of less than 15% of the composition, a nitrogen containing organic compound content of less than 20% of the composition, a protein containing organic compound content of less than 20% of the composition, a mineral content of less than 5% of the composition, a sand content of less than 5% of the composition, and a dirt content of less than 25% of the composition.

There is thus provided in accordance with yet another embodiment of the present invention a method for producing a combustion product composition from a solid portion of a sewage suspension including producing the cellulosic feedstock composition and further including at least one of the following: grinding the cellulosic feedstock, removing a protein containing organic compound from the cellulosic feedstock, removing a nitrogen containing organic compound from the cellulosic feedstock, pressing the cellulosic feedstock, at least partially drying the cellulosic feedstock, and adding oil to the cellulosic feedstock, thereby producing the combustion product composition.

There is thus provided in accordance with still another embodiment of the present invention a method for producing an ethanol containing composition from a solid portion of a sewage suspension including producing the cellulosic feedstock composition, hydrolyzing the cellulosic feedstock, and fermenting the cellulosic feedstock, thereby producing the ethanol containing composition. Accordingly, the method further includes at least one of the following: removing oil from the cellulosic feedstock, removing a protein containing organic compound from the cellulosic feedstock, removing a nitrogen containing organic compound from the cellulosic feedstock, grinding the cellulosic feedstock, at least partially sterilizing the cellulosic feedstock, and at least partially drying the cellulosic feedstock.

There is thus provided in accordance with a further embodiment of the present invention a method for producing a pulp or paper product composition from a solid portion of a sewage suspension including producing the cellulosic feedstock composition and further including at least one of the following removing oil from the cellulosic feedstock, removing a protein containing organic compound from the cellulosic feedstock, removing a nitrogen containing organic compound from the cellulosic feedstock, cleaning the cellulosic feedstock, delignifying the cellulosic feedstock, screening the cellulosic feedstock, refining the cellulosic feedstock, and at least partially drying the cellulosic feedstock, thereby producing the pulp or paper product composition.

There is thus provided in accordance with a further embodiment of the present invention a method for producing an animal feed or animal media composition from a solid portion of a sewage suspension including producing the cellulosic feedstock composition and further including at least one of the following: pressing the cellulosic feedstock, at least partially sterilizing the cellulosic feedstock, at least partially drying the cellulosic feedstock, and grinding the cellulosic feedstock, thereby producing the animal feed or animal media composition.

There is thus provided in accordance with yet a further embodiment of the present invention a method for producing a glucose containing composition from a solid portion of a sewage suspension including producing the cellulosic feedstock composition, and hydrolyzing the cellulosic feedstock, thereby producing the glucose containing composition. Accordingly, the method further includes at least one of the following: removing oil from the cellulosic feedstock, removing a protein containing organic compound from the cellulosic feedstock, removing a nitrogen containing organic compound from the cellulosic feedstock, grinding the cellulosic feedstock, at least partially sterilizing the cellulosic feedstock, and at least partially drying the cellulosic feedstock.

In accordance with an embodiment of the present invention exhausted thermal energy generated during the drying is transformed to electrical energy. Additionally, the electrical energy is provided for performing the drying. Moreover, the drying yields residual minerals and the residual minerals are used as fertilizers.

There is thus provided in accordance with still a further embodiment of the present invention a method for reducing gaseous emission from a sewage management system including removing at least 20% of a solid biomass portion of a sewage suspension which flows within the sewage management system, thereby reducing the gaseous emission. Accordingly, the removal of at least 20% of the solid biomass portion results in a reduction of at least 20% of the gaseous emission. Additionally, the reduction of the gaseous emission is comprised of at least one of the following: reduction of gaseous emission during anaerobic processing of the sewage suspension within the sewage management system following the removal of the solid biomass portion therefrom, reduction of gaseous emission during landfilling of sludge produced by processing of the sewage suspension within the sewage management system following the removal of the solid biomass portion therefrom, and reduction of gaseous emission due to reduced electricity consumption during operation of the sewage management system. Moreover, the removed solid biomass portion is processed so as to produce a combustion product for replacing fossil foils, thereby further reducing gaseous emission caused by combustion of fossil foils. Additionally, the gaseous emission includes a methane emission and a carbon dioxide emission. Accordingly, Certified Emission Reduction (CER) units are earned by the reduction of the gaseous emission.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents, and other references mentioned herein are incorporated by reference. The references cited herein are not admitted to be prior art to the claimed invention. In the case of conflict, the present specification, including definitions, will control. In addition, the materials, methods, and examples are illustrative only and are not intended to be limiting.

Other features and advantages of the invention will be apparent from the following detailed description and claims.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

Figure 1:
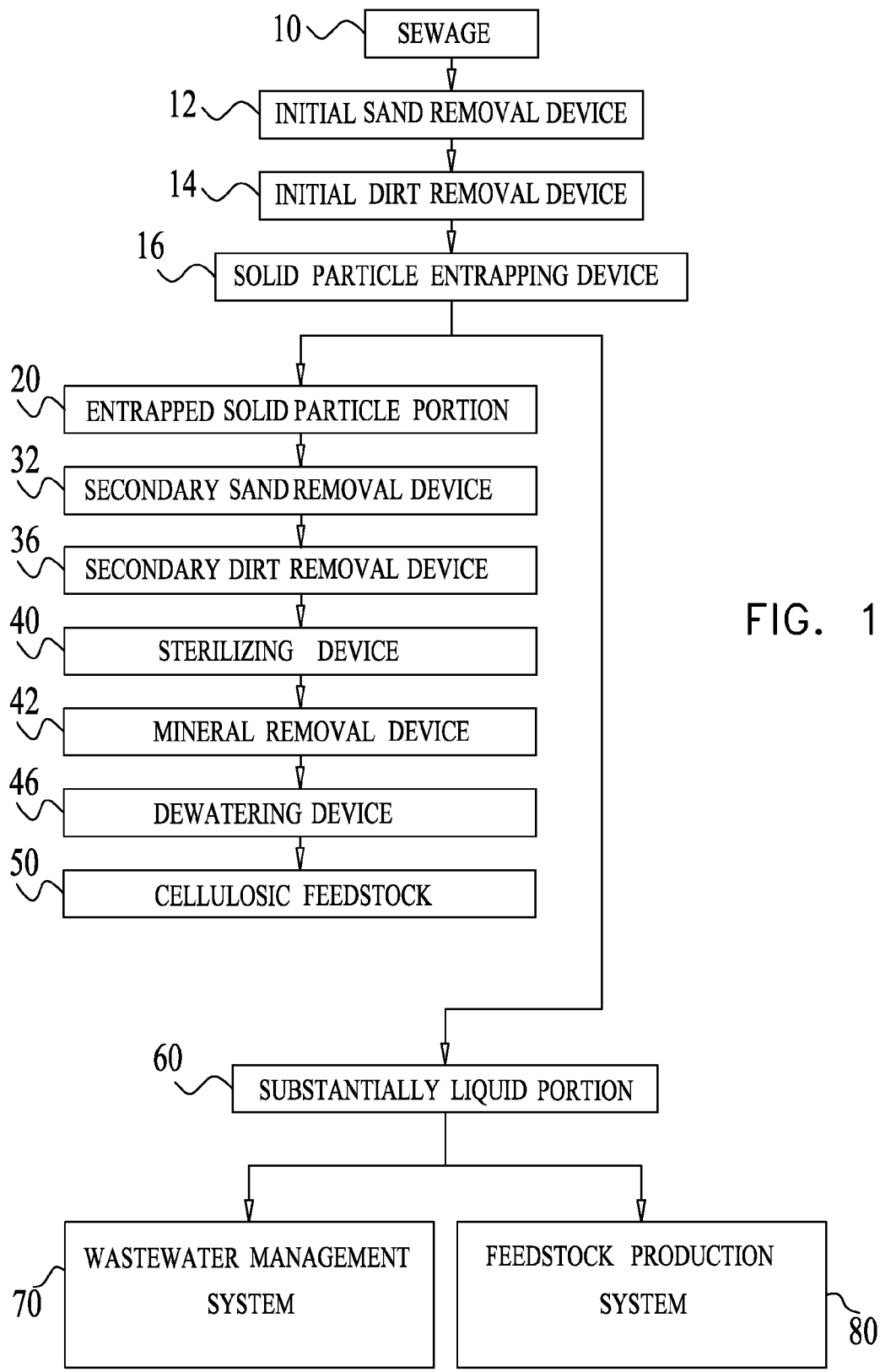
FIG. 1 is a simplified block diagram of a system for producing cellulosic feedstock from sewage, constructed and operative in accordance with an embodiment of the present invention.

Reference is now made to FIG. 1, which is a simplified block diagram of a system for producing cellulosic feedstock from sewage, constructed and operative in accordance with an embodiment of the present invention. As seen in FIG. 1, sewage 10 may be introduced into a solid portion removal device 11.

Sewage 10 may be raw sewage, i.e. a sewage stream flowing within a sewerage waste system prior to standard wastewater treatment thereof. Raw sewage may flow from a municipal sewage waste system or any other sewage system, such as, for example, industrial or agricultural waste systems.

Raw sewage of the municipal sewage waste system is generally a suspension comprising a liquid portion in a range of approximately 25-99.99% and a solid portion in a range of approximately 0.01-75% thereof. Typically, the municipal sewage waste system is a suspension comprising approximately a 75-99.99% liquid portion and approximately a 0.01-25% solid portion. The solid portion is partially suspended within the liquid portion and partially solved therein. In raw sewage the solid portion typically comprises a 50% soluble solid portion and a 50% suspended solid portion. Typically, the liquid portion comprises water, soluble organic matter, minerals, oils and other materials. The suspended solid portion of raw sewage is an aggregate of particles containing generally a cellulose content of 20-90% thereof; a hemicellulose content of 1-35% thereof; a lignin content of less than 20% thereof; a nitrogen containing organic compound content of up to 20% thereof; a protein containing organic compound content of up to 20% thereof; a mineral content of less than 15% thereof; a sand content of less than 15% thereof and a dirt content of less than 30% thereof and other sewage refuse. The solid portion may also include oil and water adsorbed to the particles. The solid portion of raw sewage typically includes less than 15% of oil therein.

It is noted that the term "oil" includes any oleaginous matter such as grease, fats and oils.

Alternatively, sewage 10 may also be treated sewage, typically treated by standard wastewater treatment thereof and may be effused into sand removal device 12 from a municipal sewage waste system, such as a Wastewater Treatment Plant (WWTP) or any location within the WWTP prior to digestion of the sewage therein.

Sewage 10 may flow into solid portion removal device 11 via a pipe or by any other suitable means.

Solid portion removal device 11 is provided to remove a substantially solid portion from the stream of sewage 10 and may include an initial sand removal device 12 operative to remove sand from sewage 10 by any suitable means. For example, sand may be removed from sewage 10 by sedimentation of the sand and thereafter discarding the sand sediment from the sand removal device 12. Sedimentation of the sand may be performed by centrifugation, such as hydrocyclonic centrifugation, vibration or ultrasonic sedimentation, for example. Sand sediment may be discarded by any suitable means, such as via a pipe affixed to the sand removal device 12. Additionally, sand may be removed by employing Dissolved Air Floation (DAF) technology.

DAF technology is a process for removal of suspended matter, such as solids or oil, from a suspension. The removal is achieved by dissolving air in the suspension under pressure and then releasing the air at atmospheric pressure in a flotation tank or basin. The released air forms tiny bubbles which adhere to the suspended matter causing the suspended matter to float to the surface of the suspension. The floating suspended matter is thereafter removed from the surface. Thus suspended sand may be removed from the sewage suspension.

Initial sand removal in sand removal device 12 may be performed as the sewage 10 is flowing. Alternatively, sand may be initially removed from sewage 10 as the sewage flow is slowed or halted and sewage 10 is thereafter introduced into a tank wherein the initial sand removal is performed.

It is appreciated that the quantity of sand within sewage 10 may vary in accordance with the climate wherein the sewage 10 is located.

The sewage 10 may be thereafter introduced into an initial dirt removal device 14 operative to remove dirt composed of components such as iron, dust, rocks, metals and plastic particles, by any suitable means. For example, dirt may be removed by sedimentation of the dirt and thereafter discarding the dirt sediment from the dirt removal device 14. Sedimentation of the dirt may be performed by centrifugation, such as hydrocyclonic centrifugation, vibration or ultrasonic sedimentation, for example. Dirt sediment may be discarded by any suitable means, such as via a pipe affixed to the dirt removal device 14. Additionally, dirt may be removed by employing DAF technology.

Iron or other metals may be removed by any suitable means, such as by utilizing a magnet which attracts the iron thereto thus removing a portion of the iron or other metals from the sewage 10.

Moreover, relatively light dirt components, such as dust, may be removed by sedimentation as described hereinabove, or by suspending the dirt components and thereafter discarding the dirt suspension from the dirt removal device 14. Relatively heavy dirt components, such as metals, may be removed by sedimentation as described hereinabove.

Sewage 10 is introduced into a solid particle entrapping device 16. Entrapping device 16 may be comprised of a single net or a multiplicity of nettings for entrapping the solid portion of sewage 10. The multiplicity of nettings may be a series of nettings wherein each subsequent netting is formed with apertures of a smaller size than the previous netting so as to provide additional trapping of solid particles from the sewage 10. A netting mesh may be substantially in the range of 80-500 microns, for example.

The nettings may be formed in any suitable configuration and may be formed of any suitable material such as a corrosive resistive material and/or a high pressure resistive material, typically aluminum, for example.

It is appreciated that retrieval and entrapping of solid particles from sewage 10 may be achieved in any suitable manner, such as by employing DAF technology; by separation with conveyor belts formed of conveyor belt mesh; centrifugation, such as flow centrifugation or hydrocyclonic centrifugation, for example; separation by screw presses; separation by use of vibration in a vibration separator; filtering by disk filters, filter presses, media filters, such as filters containing fibers, for example, biological filters, such as filters containing cellulose, for example, chemical filters, such as filters containing silica, for example, a filter employing backflushing technology, or any other suitable manner for entrapping solids from sewage 10. A backflushing filter may be commercially available from the Salsnes Filter AS company of 279 Postboks, Namsos 7801, Norway, under the catalogue number of SF 6000.

A backflushing filter comprises a screen or a filtration media operative to filter solids such that solids accumulate on a first surface of the screen or filtration media. Liquid, generally water, is urged to flow from an opposite surface of the screen or filtration media to the first surface thereof. This reverse flow of liquid through the screen or filtration media is used for removing solids accumulated on the screen or filtration media during the filtration process.

A pressure device, such as a pump or a water jet, may be engaged with entrapping device 16. The pressure device is operative to ensure sewage 10 flows unhindered through entrapping device 16, such as by declogging oils and plastic particles accumulated on the net of entrapping device 16. Furthermore, a resulting entrapped solid particle portion 20, trapped by entrapping device 16, may be cleaved by application of pressure by the pressure device thereon. The pressure applied by the pressure device is typically in the range of 10-200 Atm, for example.

A vibration element, such as springs, may be provided to enhance flow of sewage 10 within entrapping device 16.

The entrapped solid particle portion 20 of entrapping device 16 is comprised of solid particles and liquids adsorbed to the solid particles, such as oils and water. Generally the solid particles of entrapped solid particle portion 20 exceed a size of approximately 80 microns. Typically, entrapped solid particle portion 20 comprises 10%-90% of the solids from sewage 10 and includes 20%-95% organic fibers.

It is noted that the term "size" may include any applicable parameter, such as a particle length or a particle diameter, for example.

Entrapped solid particle portion 20 may be removed from entrapping device 16 in any suitable manner, such as via conveyer belts, conduits or spiral cams, for example.

In a non-limiting example, a yield of 1 ton of cellulose of the solid particle portion 20 is obtained from processing 3300 $m^3$ of sewage 10 within entrapping device 16 and an amount of 15,000 $m^3$ of cellulose of the solid particle portion 20 is obtained per day.

The entrapped solid portion 20 may be introduced into a secondary sand removal device 32 for further removal of sand within entrapped solid portion 20 by any suitable means. Secondary sand removal device 32 may be formed of any one of the abovementioned apparati forming initial sand removal device 12.

In a non-limiting example, initial sand removal device 12 and secondary sand removal device 32 are operative to remove the sand content such that approximately less than 5% sand content remains within entrapped solid portion 20.

The entrapped solid portion 20 may be introduced into a secondary dirt removal device 36 for further removal of dirt within entrapped solid portion 20 by any suitable means. Secondary dirt removal device 36 may be formed of any one of the abovementioned apparati forming initial dirt removal device 14.

In a non-limiting example, initial dirt removal device 14 and secondary dirt removal device 36 are operative to remove the dirt content such that approximately less than 25% dirt content remains in entrapped solid portion 20.

The entrapped solid portion 20 may be introduced into a sterilizing device 40 for sterilizing entrapped solid portion 20. Sterilizing device 40 may employ any suitable method for sterilizing the solid portion 20, such as steam sterilization, UV sterilization or use of a chemical reagent for sterilization, for example. Alternatively, the entrapped solid portion 20 may be partially sterilized, such as by being introduced into a pasteurization device for pasteurizing the entrapped solid portion 20.

The entrapped solid portion 20 may be introduced into a mineral removal device 42 for removal of minerals, typically ash and salts, therefrom, by any suitable means. For example, minerals may be removed by washing the entrapped solid portion 20, such as by washing with a deionized water wash, a chemical wash, such as a hydrochloric acid wash and/or use of steam.

In a non-limiting example, mineral removal device 42 is operative to remove the mineral content such that approximately less than 5% mineral content remains in entrapped solid portion 20.

The entrapped solid portion 20 may be introduced into a dewatering device 46 for removing a portion of water from solid portion 20. Dewatering device 46 may employ any suitable method for removing water from the solid portion 20, such as by evaporation employing heat treatment, such as use of solar heat or greenhouse heat, for example, cryogenic treatment, vacuum, a press, such as a screw press, a drum dryer or a combination thereof.

A resultant cellulosic feedstock composition 50 is thus produced from sewage 10.

It is appreciated that the order of using the devices described hereinabove may be alternated so as to produce cellulosic feedstock 50 from sewage 10. A skilled artisan will appreciate that in the process of producing cellulosic feedstock 50 some of the devices described hereinabove may be obviated without compromising the quality of the produced cellulosic feedstock 50.

Cellulosic feedstock 50 may be used to manufacture a plurality of materials, such as, without limiting: textile; combustion products, such as wood pellets, wood chips; fiberboards; plant media; pulp; paper; animal feed; animal media, glucose and biofuels, such as butanol, propane butane and ethanol, for example.

The cellulosic feedstock 50 is a composition substantially comprising an oil content of up to 15% thereof; a cellulose content of 40-99% thereof; a hemicellulose content of 2-20% thereof; a lignin content of less than 15% thereof a nitrogen containing organic compound content of up to 20% thereof; and a protein containing organic compound content of up to 20% thereof; a mineral content of less than 5% thereof; a sand content of less than 5% thereof and a dirt content of less than 25% thereof. The cellulosic feedstock 50 may comprise particles with a size of 0.01 microns-100 mm. The caloric value of the cellulosic feedstock 50 may be in the range of 5000-16000 British Thermal Units (BTU)/Pound.

It is noted that the oil content may be an oil content of up to 1% thereof, an oil content of up to 2% thereof, an oil content of up to 3% thereof, an oil content of up to 4% thereof, an oil content of up to 5% thereof, an oil content of up to 6% thereof, an oil content of up to 7% thereof, an oil content of up to 8% thereof, an oil content of up to 9% thereof, an oil content of up to 10% thereof, an oil content of up to 11% thereof, an oil content of up to 12% thereof, an oil content of up to 13% thereof, an oil content of up to 14% thereof or an oil content of up to 15% thereof.

The cellulose content may be a cellulose content of 40-45% thereof, a cellulose content of 50-55% thereof, a cellulose content of 55-60% thereof, a cellulose content of 60-65% thereof, a cellulose content of 65-70% thereof, a cellulose content of 70-75% thereof, a cellulose content of 75-80% thereof, a cellulose content of 80-85% thereof, a cellulose content of 85-90% thereof, a cellulose content of 90-95% thereof or a cellulose content of 95-99% thereof.

The hemicellulose content may be a hemicellulose content of 2% thereof, a hemicellulose content of 2-3% thereof, a hemicellulose content of 2-4% thereof, a hemicellulose content of 2-5% thereof; a hemicellulose content of 2-6% thereof, a hemicellulose content of 2-7% thereof, a hemicellulose content of 2-8% thereof, a hemicellulose content of 2-9% thereof, a hemicellulose content of 2-10% thereof, a hemicellulose content of 2-11% thereof, a hemicellulose content of 2-12% thereof, a hemicellulose content of 2-13% thereof, a hemicellulose content of 2-14% thereof, a hemicellulose content of 2-15% thereof, a hemicellulose content of 2-16% thereof, a hemicellulose content of 2-17% thereof, a hemicellulose content of 2-18% thereof, a hemicellulose content of 2-19% thereof or a hemicellulose content of 20% thereof.

The lignin content may be a lignin content of less than 15% thereof, a lignin content of less than 14% thereof, a lignin content of less than 13% thereof, a lignin content of less than 12% thereof, a lignin content of less than 11% thereof, a lignin content of less than 10% thereof, a lignin content of less than 9% thereof, a lignin content of less than 8% thereof, a lignin content of less than 7% thereof, a lignin content of less than 6% thereof, a lignin content of less than 5% thereof, a lignin content of less than 4% thereof, a lignin content of less than 3% thereof, a lignin content of less than 2% thereof or a lignin content of less than 1% thereof.

The nitrogen containing organic compound content may be a content of up to 1% thereof, a nitrogen containing organic compound content of up to 2% thereof, a nitrogen containing organic compound content of up to 3% thereof, a nitrogen containing organic compound content of up to 4% thereof, a nitrogen containing organic compound content of up to 5% thereof, a nitrogen containing organic compound content of up to 6% thereof, a nitrogen containing organic compound content of up to 7% thereof, a nitrogen containing organic compound content of up to 8% thereof, a nitrogen containing organic compound content of up to 9% thereof, a nitrogen containing organic compound content of up to 10% thereof, a nitrogen containing organic compound content of up to 11% thereof, a nitrogen containing organic compound content of up to 12% thereof, a nitrogen containing organic compound content of up to 13% thereof, a nitrogen containing organic compound content of up to 14% thereof, a nitrogen containing organic compound content of up to 15% thereof, a nitrogen containing organic compound content of up to 16% thereof, a nitrogen containing organic compound content of up to 17% thereof, a nitrogen containing organic compound content of up to 18% thereof, a nitrogen containing organic compound content of up to 19% thereof or a nitrogen containing organic compound content of up to 20% thereof.

The protein containing organic compound content may be a content of up to 1% thereof, a protein containing organic compound content of up to 2% thereof, a protein containing organic compound content of up to 3% thereof, a protein containing organic compound content of up to 4% thereof, a protein containing organic compound content of up to 5% thereof, a protein containing organic compound content of up to 6% thereof, a protein containing organic compound content of up to 7% thereof, a protein containing organic compound content of up to 8% thereof, a protein containing organic compound content of up to 9% thereof, a protein containing organic compound content of up to 10% thereof, a protein containing organic compound content of up to 11% thereof, a protein containing organic compound content of up to 12% thereof, a protein containing organic compound content of up to 13% thereof, a protein containing organic compound content of up to 14% thereof, a protein containing organic compound content of up to 15% thereof, a protein containing organic compound content of up to 16% thereof, a protein containing organic compound content of up to 17% thereof, a protein containing organic compound content of up to 18% thereof, a protein containing organic compound content of up to 19% thereof or a protein containing organic compound content of up to 20% thereof.

The sand content may be less than 5% thereof, less than 4% thereof, less than 3% thereof, less than 2% thereof, less than 1% thereof or less than 0.5% thereof. The mineral content may be less than 5% thereof, less than 4% thereof, less than 3% thereof, less than 2% thereof, less than 1% thereof or less than 0.5% thereof. The dirt content may be less than 25% thereof, less than 20% thereof, less than 15% thereof, less than 10% thereof, less than 5% thereof or less than 1% thereof.

The cellulosic feedstock 50 may comprise particles with a size of 0.01-1 microns, a size of 1-5 microns, a size of 5-10 microns, a size of 10-20 microns, a size of 20-30 microns, a size of 30-40 microns, a size of 40-50 microns, a size of 50-60 microns, a size of 60-70 microns, a size of 70-80 microns, a size of 80-90 microns, a size of 90-100 microns, a size of 100-150 microns, a size of 150-200 microns, a size of 200-250 microns, a size of 250-300 microns, a size of 300-350 microns, a size of 350-400 microns, a size of 400-450 microns, a size of 450-500 microns, a size of 500-550 microns, a size of 550-600 microns, a size of 600-650 microns, a size of 650-700 microns, a size of 750-800 microns, a size of 800-850 microns, a size of 850-900 microns, a size of 900-950 microns, a size of 950-1000 microns, a size of 1-5 mm, a size of 5-10 mm, a size of 10-15 mm, a size of 15-20 mm, a size of 20-25 mm, a size of 25-30 mm, a size of 30-35 mm, a size of 35-40 mm, a size of 40-45 mm, a size of 45-50 mm, a size of 50-55 mm, a size of 55-60 mm, a size of 60-65 mm, a size of 65-70 mm, a size of 70-75 mm, a size of 75-80 mm, a size of 80-85 mm, a size of 85-90 mm, a size of 90-95 mm or a size of 95-100 mm.

The caloric value of the cellulosic feedstock 50 may be in the range of 5000-6000 BTU/Pound; in the range of 6000-7000 BTU/Pound; in the range of 7000-8000 BTU/Pound; in the range of 8000-9000 BTU/Pound; in the range of 9000-10000 BTU/Pound; in the range of 10000-11000 BTU/Pound; in the range of 11000-12000 BTU/Pound; in the range of 12000-13000 BTU/Pound; in the range of 13000-14000 BTU/Pound; in the range of 14000-15000 BTU/Pound or in the range of 15000-16000 BTU/Pound.

A residual, substantially liquid portion 60, discharged from entrapping device 16, comprises the liquid portion of sewage 10 and relatively small solid particles, typically particles with a size of less than approximately 80 microns. Liquid portion 60 may be discarded or may flow to a wastewater management system 70, such as back to the municipal sewage waste system, such as to the WWTP or any location prior to digestion within the WWTP, for example, in any suitable manner, such as by conduits. Alternatively, liquid portion 60 may be introduced into an additional feedstock production system 80 for producing additional feedstock from sewage 10.

It is appreciated that producing the cellulosic feedstock 50 according to the methods described hereinabove provides for a plurality of superior benefits. For example, the entrapped solid particle portion 20 obtained from sewage has relatively less lignin in comparison with solids retrieved from vegetative sources, such as, wood, wheat and corn. In a non-limiting example, entrapped solid particle portion 20 retrieved from sewage 10 contains 30%-60% less lignin than solids retrieved from corn. Thus use of entrapped solid particle portion 20 retrieved from sewage 10 allows for producing cellulosic feedstock 50 with a relatively small volume of lignin. This may be advantages in production of various products, such as a paper product from the cellulosic feedstock since the quality of the paper product increases as the lignin volume decreases therein.

An additional benefit is that fibers of entrapped solid particle portion 20 have a larger total surface area than fibers retrieved from vegetative sources. This is due to disintegration of the fibers within the sewage 10 and due to cleaving of fibers by urging of the pressure device thereon. Thus use of fibers of entrapped solid particle portion 20 enhances the efficiency of feedstock production due to the relatively large fiber surface area, which allows for increased contact with processing materials, such as contact with a hydrochloric acid wash for manufacturing products from the cellulosic feedstock 50, for example.

Another benefit is that fibers of entrapped solid particle portion 20 obtained from sewage have a relatively high cellulose content, as described hereinabove, thus allowing for production of high quality products therefrom. For example, glucose and ethanol, which comprise mainly cellulose, may be produced from the cellulosic feedstock 50.

Conventionally following treatment of sewage 10 in a wastewater management system, typically a WWTP, the volume of solids within the sewage 10 is reduced. For example, the volume of solids within the sewage 10 is conventionally reduced by 30-40% due to processing within a digestion tank in the WWTP in systems wherein the solid portion removal device 11 is not employed. Processing of the sewage 10 produces sludge. Typically, sludge is disposed of by drying and landfilling thereafter.

It is a particular feature of the present invention that solids of the sewage 10 are removed from sewage 10 prior to entering the digestion tank within the WWTP. Removal of solids from sewage 10 may be performed prior to entering a primary sedimentation tank within the WWTP. This allows for maximal removal of solids from sewage 10 prior to settling of solids within the sedimentation tank.

Removal of solids from the sewage 10 decreases the volume of the solid components to be digested or processed within the WWTP. For example, introducing sewage 10 into solid portion removal device 11 may bring to a volume reduction of the solids within the remaining liquid portion 60 of sewage 10. Thus removing the solids from the sewage according to the methods described hereinabove provides an additional benefit by decreasing the solid volume to be processed within the WWTP.

It is further appreciated that by removal of the suspended solid portion of the sewage 10 a substantial portion of digestion resistant components, such as cellulose, minerals and sand, comprised within the suspended solid portion, are removed thereby. Removal of the digestion resistant components from sewage 10 prior to introduction into a digestion tank of the WWTP, provides for increased digestion efficiency within the digestion tank and thus a substantially decreased volume of sludge is produced in comparison with the volume of sludge produced within a standard WWTP, wherein solids are not removed.

The following example illustrates the effect of the increased digestion efficiency on the volume of sludge produced by digestion of the remaining liquid portion 60 of sewage 10 within the WWTP. In raw sewage the total solid portion typically comprises a 50% soluble solid portion and a 50% suspended solid portion. By removing 50% of the suspended solid portion the remaining liquid portion 60 of sewage 10 now contains a solid portion comprising a 75% soluble solid portion and a 25% suspended solid portion. It would have been expected that as a result of removing 50% of the suspended solid portion, i.e. 25% of the total solid portion, the sludge volume would accordingly be reduced by 25%. Rather it has been found that by removing 50% of the suspended solid portion the digestion efficiency of remaining liquid portion 60 is increased at least twofold thus reducing the produced sludge volume by at least 50%. Thus removing the solids from the sewage according to the methods described hereinabove provides an additional benefit by significantly decreasing the solid volume to be processed within the WWTP.

An additional benefit is that increased digestion efficiency within the digestion tank allows for a relatively simple digestion process which does not require introduction of polymers, such as coagulants and flocculents into the digestion tank, as generally required to facilitate digestion in standard WWTP. Additionally, significantly less bacteria is necessary to facilitate digestion. Less polymers and bacteria allow for significantly increased efficiency in dewatering the sludge produced within the WWTP.

In a non limiting example, sludge processed in a WWTP wherein the solids were removed prior to digestion thereof, contains 10% less bacteria than sludge processed in a standard WWTP without prior removal of solids therefrom.

Additionally, in a not limiting example, 60-97% of water may be removed from sludge processed in a WWTP wherein the solids were removed prior to digestion thereof, while only 15-22% of water is typically removed from sludge processed in a standard WWTP without prior removal of solids therefrom.

It is further appreciated that the liquid portion 60 that is discarded prior to introduction within a WWTP or following production of sludge therefrom within the WWTP is less harmful to the environment and specifically to the ground due to, inter alia, decreased volume of polymers and bacteria. Additionally, as described hereinabove, a portion of oil is removed from sewage 10 while removing solids therefrom. Thus, decreasing the hydrophobic properties of the liquid portion 60 and allowing the liquid portion 60 to be absorbed within the ground when discarded. Additionally the liquid portion 60 has less soluble solids therein thereby decreasing the pollutants introduced into the environment and specifically to the ground.

Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

Examples 1 and 2 describe producing cellulosic feedstock 50 from sewage 10 in the system described in reference to FIG. 1.

Example 1

Figure 2:
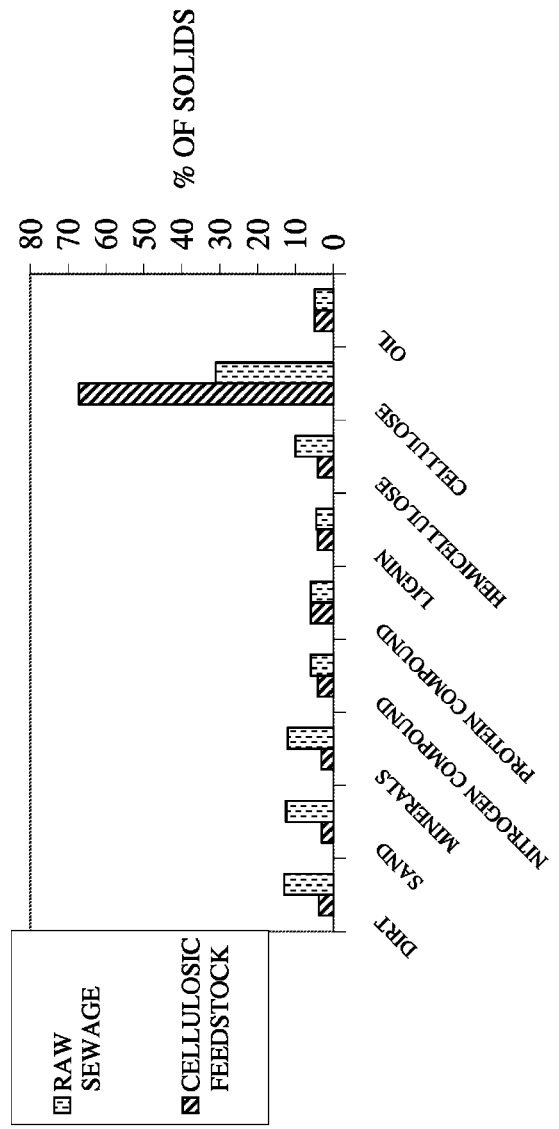
FIG. 2 is a graph of a solid composition obtained from raw sewage Vs. a cellulosic feedstock composition processed in the system of FIG. 1.

Experimental Procedure 100 m$^3$ of raw sewage, including a solid portion of approximately 0.1% of the raw sewage, was obtained from a municipal sewage waste system. As seen in FIG. 2, the composition of the raw sewage solid portion generally comprises 5% oil, 31% cellulose, 10% hemicellulose, 4.5% lignin, 6% protein containing organic compound, 6% nitrogen containing organic compound, 12.1% minerals, 12.5% sand and 12.9% dirt.

The raw sewage was introduced into a hydrocyclone centrifuge at a pressure of 3 Atm for initial sand and dirt removal from the raw sewage. The remaining portion was introduced into a magnet containing device wherein a portion of iron was magnetically removed.

Thereafter the raw sewage was introduced into an entrapping device formed of a net of a 250 micron mesh. Approximately 50 Kg of solids were entrapped within the net. The residual liquid portion was discarded.

Secondary sand removal was performed by sedimentation in a conical-shaped pool wherein the sand sunk to the bottom of the pool. The sedimented sand was discarded.

The solid portion was introduced into a sterilizer at a temperature of 85° C. for 10 minutes.

Mineral removal was performed by use of a chemical wash wherein the solid portion was boiled at 85° C. for one hour with a solution of distilled water mixed with a 37% hydrochloric acid in a boiling apparatus. The boiled solid portion was thereafter washed 2 times with deionized water.

The solid portion was pressed in a screw press for partial removal of liquids therefrom.

Experimental Results:

As seen in FIG. 2, a resulting cellulosic feedstock composition was produced in the system described hereinabove wherein the cellulosic feedstock composition generally comprises 5% oil, 67.1% cellulose, 4% hemicellulose, 4% lignin, 6% protein containing organic compound, 4% nitrogen containing organic compound, 3.1% minerals, 3% sand and 3.8% dirt.

Example 2

Figure 3:
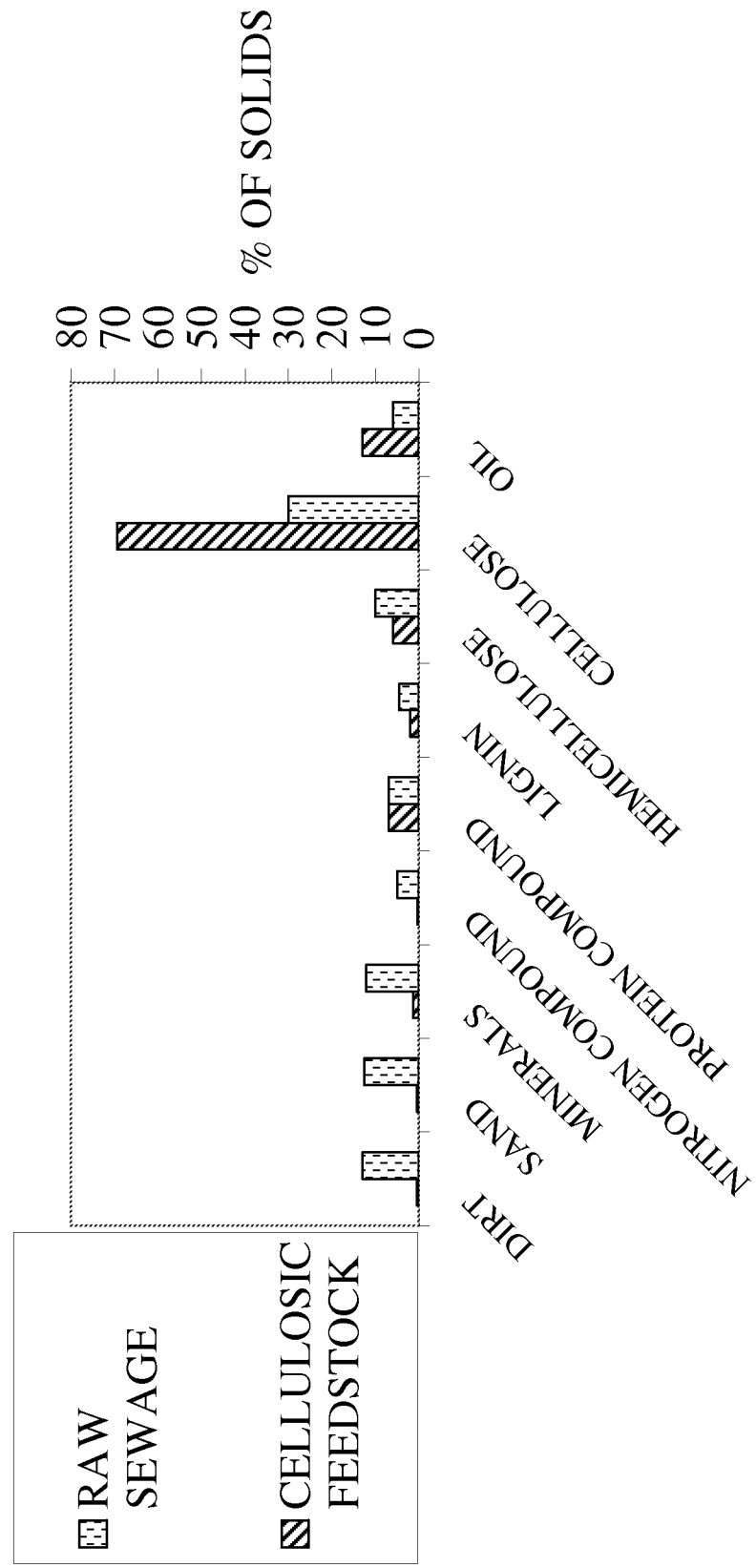
FIG. 3 is a graph of an additional solid composition obtained from raw sewage Vs. a cellulosic feedstock composition processed in the system of FIG. 1.

Experimental Procedure 120 m³ of raw sewage, including a solid portion of approximately 0.05% of the raw sewage, was obtained from a municipal sewage waste system. As seen in FIG. 3, the composition of the raw sewage solid portion generally comprises 6% oil, 30% cellulose, 10% hemicellulose, 4.5% lignin, 7% protein containing organic compound, 5% nitrogen containing organic compound, 12.1% minerals, 12.5% sand and 12.9% dirt.

The raw sewage was introduced into a hydrocyclone centrifuge at a pressure of 3 Atm for initial sand and dirt removal from the raw sewage.

Thereafter the raw sewage was introduced into a vibration separator commercially available from the Sewco company of 8029 US Highway 25 Florence, Ky., USA under catalogue model SS of Sanitary Separators for entrapping solids therein by use of vibration. The residual liquid portion was discarded.

Secondary sand removal was performed by sedimentation in a conical-shaped pool wherein the sand sunk to the bottom of the pool. The sedimented sand was discarded.

The solid portion was pasteurized in a pasteurization device at a temperature of 72° C. for two minutes for partial sterilization thereof.

Mineral removal was performed by use of a chemical wash wherein the solid portion was washed with a solution of distilled water mixed with a 2% hydrochloric acid. The solid portion was thereafter washed with soft water.

The solid portion was pressed in a screw press for partial removal of liquids therefrom.

Experimental Results:

As seen in FIG. 3, a resulting cellulosic feedstock composition was produced in the system described hereinabove wherein the cellulosic feedstock composition generally comprises 13% oil, 69.4% cellulose, 6% hemicellulose, 2% lignin, 7% protein containing organic compound, 0.3% nitrogen containing organic compound, 1.3% minerals, 0.5% sand and 0.5% dirt.

Figure 4:
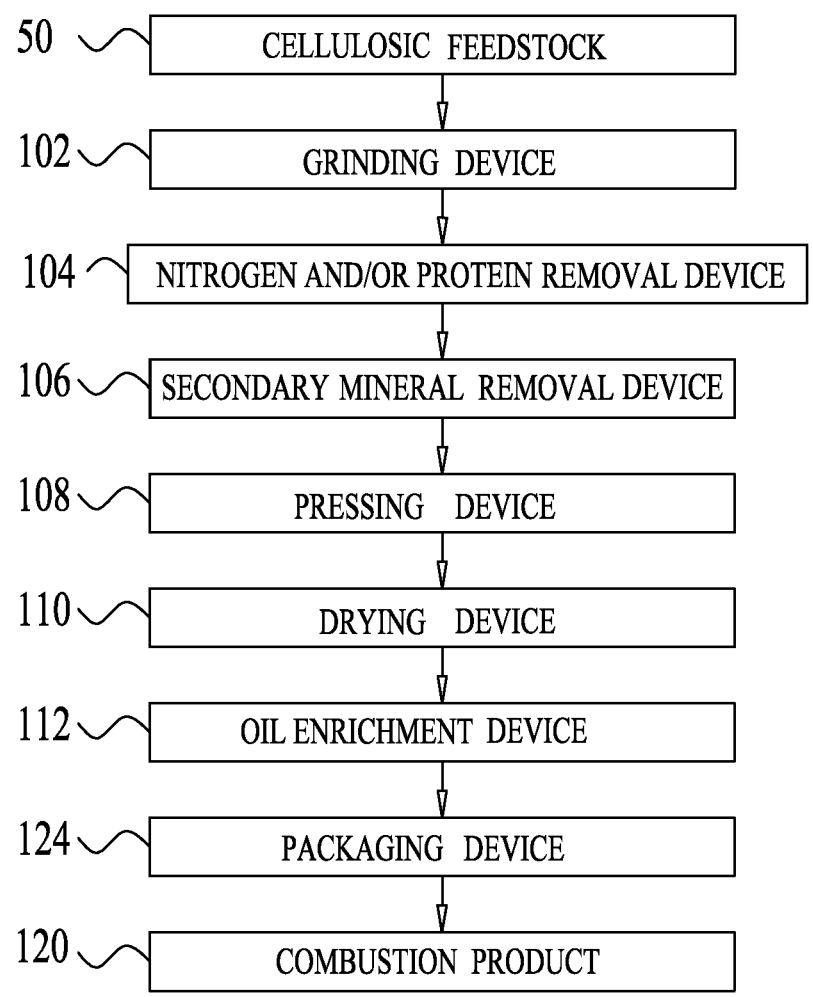
FIG. 4 is a simplified block diagram of a system for manufacturing a cellulosic product from cellulosic feedstock, constructed and operative in accordance with an embodiment of the present invention.

Reference is now made to FIG. 4, which is a simplified block diagram of a system for manufacturing a combustion product from cellulosic feedstock, constructed and operative in accordance with an embodiment of the present invention. As seen in FIG. 4, the cellulosic feedstock 50 may be ground in a grinding device 102 by any suitable means, such as by employment of a screw press, a filter or a blender, a ball grinder, a stone or knife grinder, for example. The cellulosic feedstock 50 may be ground to any suitable particle size, such as to particles with a size of approximately less than 1 mm, for example.

The cellulosic feedstock 50 may be introduced into a nitrogen and/or protein removal device 104 for removal of a portion of the nitrogen and protein containing compounds by any suitable means, such as by pH Gradient Electrophoresis employing acid washes, such as a hydrogen chloride (HCl) wash, a dihydrogen phosphate ($H_2PO_4$) wash or a sodium hydroxide (NaOH) wash, for example.

The cellulosic feedstock 50 may be introduced into a secondary mineral removal device 106 for further removal of minerals within cellulosic feedstock 50 by any suitable means. Secondary mineral removal device 106 may be formed of any one of the abovementioned apparati forming mineral removal device 42 of FIG. 1.

The cellulosic feedstock 50 may be thereafter pressed in a pressing device 108 employing any suitable means, such use of a screw press or a filter press, a piston press, a belt press or a centrifuge for example.

The cellulosic feedstock 50 may be introduced into a drying device 110 for at least partially drying cellulosic feedstock 50. Drying device 110 may employ any suitable method for partially drying the cellulosic feedstock 50, such as drying by evaporation employing heat treatment, such as solar heat or placing the cellulosic feedstock 50 in a greenhouse, cryogenic treatment, vacuum, a press, such as a screw press, a drum dryer or a combination thereof.

The cellulosic feedstock 50 may be introduced into an oil enrichment device 112 operative to introduce any suitable oil into the cellulosic feedstock 50.

Thereafter a resultant combustion product 120 may be packaged in a packaging device 124 by any suitable means, such as by employing vacuum packing or pellet packing in a pellet machine, for example.

It is appreciated that the order of using the devices described hereinabove may be alternated so as to produce combustion product 120 from cellulosic feedstock 50.

A skilled artisan will appreciate that in the process of producing combustion product 120 some of the devices described hereinabove may be obviated without compromising the quality of the produced combustion product 120.

The resulting combustion product 120 is obtained from the system described hereinabove. The combustion product 120 is a composition substantially comprising an oil content of 1-15% thereof a cellulose content of 40-90% thereof; a hemicellulose content of 2-20% thereof; a lignin content of less than 12% thereof; a nitrogen containing organic compound content of up to 15% thereof; a protein containing organic compound content of up to 15% thereof; a sand content of less than 5% thereof; a mineral content of less than 5% thereof and a dirt content of less than 5% thereof. It is noted that the oil in the combustion product 120 enhances the combustion process. The combustion product 120 is used for combustion of materials and may be used, for example, instead of coal.

It is noted that the oil content may be an oil content of 1-15% thereof, an oil content of 1% thereof, an oil content of 1-2% thereof, an oil content of 1-3% thereof, an oil content of 1-4% thereof, an oil content 1-5% thereof, an oil content of 1-6% thereof, an oil content of 1-7% thereof, an oil content of 1-8% thereof, an oil content of 1-9% thereof, an oil content of 1-10% thereof, an oil content of 1-11% thereof, an oil content of 1-12% thereof, an oil content of 1-13% thereof, an oil content of 1-14% thereof or an oil content of 15% thereof.

The cellulose content may be a cellulose content of 40-45% thereof, a cellulose content of 45-50% thereof, a cellulose content of 50-55% thereof, a cellulose content of 55-60% thereof, a cellulose content of 60-65% thereof, a cellulose content of 65-70% thereof, a cellulose content of 70-75% thereof, a cellulose content of 75-80% thereof, a cellulose content of 80-85% thereof or a cellulose content of 85-90% thereof.

The hemicellulose content may be a hemicellulose content of 2% thereof, a hemicellulose content of 2-3% thereof, a hemicellulose content of 2-4% thereof, a hemicellulose content of 2-5% thereof; a hemicellulose content of 2-6% thereof, a hemicellulose content of 2-7% thereof, a hemicellulose content of 2-8% thereof, a hemicellulose content of 2-9% thereof, a hemicellulose content of 2-10% thereof, a hemicellulose content of 2-11% thereof, a hemicellulose content of 2-12% thereof, a hemicellulose content of 2-13% thereof, a hemicellulose content of 2-14% thereof, a hemicellulose content of 2-15% thereof, a hemicellulose content of 2-16% thereof, a hemicellulose content of 2-17% thereof, a hemicellulose content of 2-18% thereof, a hemicellulose content of 2-19% thereof or a hemicellulose content of 20% thereof.

The lignin content may be a lignin content of less than 12% thereof, a lignin content of less than 11% thereof, a lignin content of less than 10% thereof, a lignin content of less than 9% thereof, a lignin content of less than 8% thereof, a lignin content of less than 7% thereof, a lignin content of less than 6% thereof, a lignin content of less than 5% thereof, a lignin content of less than 4% thereof, a lignin content of less than 3% thereof, a lignin content of less than 2% thereof or a lignin content of less than 1% thereof.

The nitrogen containing organic compound content may be a content of up to 1% thereof, a nitrogen containing organic compound content of up to 2% thereof, a nitrogen containing organic compound content of up to 3% thereof, a nitrogen containing organic compound content of up to 4% thereof, a nitrogen containing organic compound content of up to 5% thereof, a nitrogen containing organic compound content of up to 6% thereof, a nitrogen containing organic compound content of up to 7% thereof, a nitrogen containing organic compound content of up to 8% thereof, a nitrogen containing organic compound content of up to 9% thereof, a nitrogen containing organic compound content of up to 10% thereof, a nitrogen containing organic compound content of up to 11% thereof, a nitrogen containing organic compound content of up to 12% thereof, a nitrogen containing organic compound content of up to 13% thereof, a nitrogen containing organic compound content of up to 14% thereof or a nitrogen containing organic compound content of up to 15% thereof.

The protein containing organic compound content may be a content of up to 1% thereof, a protein containing organic compound content of up to 2% thereof, a protein containing organic compound content of up to 3% thereof, a protein containing organic compound content of up to 4% thereof, a protein containing organic compound content of up to 5% thereof, a protein containing organic compound content of up to 6% thereof, a protein containing organic compound content of up to 7% thereof, a protein containing organic compound content of up to 8% thereof, a protein containing organic compound content of up to 9% thereof, a protein containing organic compound content of up to 10% thereof, a protein containing organic compound content of up to 11% thereof, a protein containing organic compound content of up to 12% thereof, a protein containing organic compound content of up to 13% thereof, a protein containing organic compound content of up to 14% thereof or a protein containing organic compound content of up to 15% thereof.

The sand content may be less than 5% thereof, less than 4% thereof, less than 3% thereof, less than 2% thereof, less than 1% thereof or less than 0.5% thereof. The mineral content may be less than 5% thereof, less than 4% thereof, less than 3% thereof, less than 2% thereof, less than 1% thereof or less than 0.5% thereof. The dirt content may be less than 5% thereof, less than 4% thereof, less than 3% thereof, less than 2% thereof, less than 1% thereof or less than 0.5% thereof.

The caloric value of the combustion product 120 may be in the range of 5000-16000 BTU/Pound. It is noted that the caloric value of the combustion product 120 may be in the range of 5000-6000 BTU/Pound; in the range of 6000-7000 BTU/Pound; in the range of 7000-8000 BTU/Pound; in the range of 8000-9000 BTU/Pound; in the range of 9000-10000 BTU/Pound; in the range of 10000-11000 BTU/Pound; in the range of 11000-12000 BTU/Pound; in the range of 12000-13000 BTU/Pound; in the range of 13000-14000 BTU/Pound; in the range of 14000-15000 BTU/Pound or in the range of 15000-16000 BTU/Pound.

Examples 3 and 4 describe producing combustion product 120 from sewage 10 in the system described in reference to FIGS. 1 and 4.

Example 3

Figure 5:
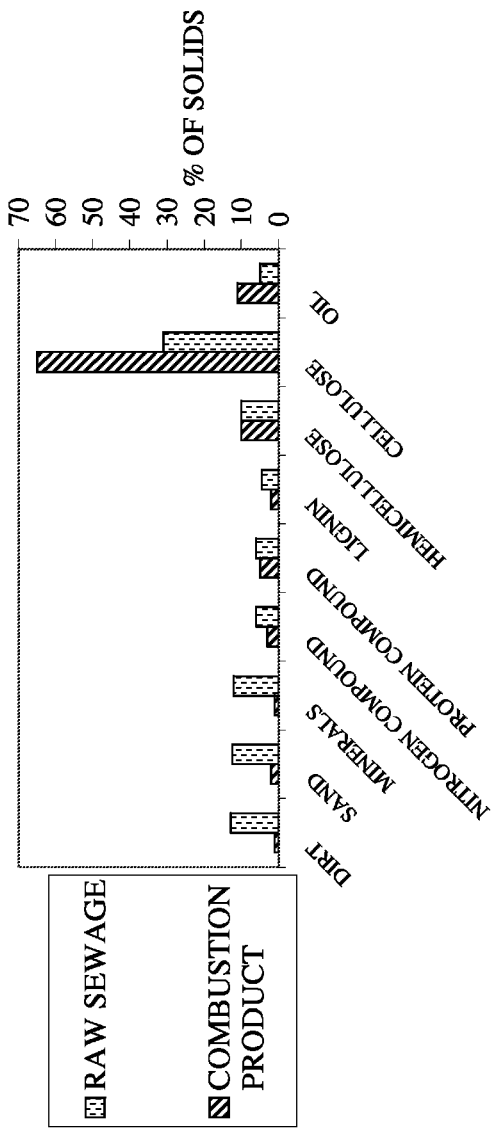
FIG. 5 is a graph of a solid composition obtained from raw sewage Vs. a cellulosic product composition processed in the systems of FIG. 1 and FIG. 4.

Experimental Procedure 100 m$^3$ of raw sewage, including a solid portion of approximately 0.1% of the raw sewage, was obtained from a municipal sewage waste system. As seen in FIG. 5, the composition of the raw sewage solid portion generally comprises 5% oil, 31% cellulose, 10% hemicellulose, 4.5% lignin, 6% protein containing organic compound, 6% nitrogen containing organic compound, 12.1% minerals, 12.5% sand and 12.9% dirt.

The raw sewage was introduced into a hydrocyclone centrifuge at a pressure of 3 Atm for initial sand removal from the raw sewage.

Thereafter the raw sewage was introduced into an entrapping device formed of a net of a 250 micron mesh. Approximately 50 Kg of solids were entrapped within the net. The residual liquid portion was discarded.

Secondary sand removal was performed by sedimentation in a conical-shaped pool wherein the sand sunk to the bottom of the pool. The sedimented sand was discarded.

Dirt removal was performed thereafter in a hydrocyclone centrifuge at a pressure of 3 Atm. The remaining portion was introduced into a magnet containing device wherein a portion of iron was magnetically removed.

The solid portion was introduced into a sterilizer at a temperature of 85° C. for 10 minutes.

Mineral removal was performed by use of a chemical wash wherein the solid portion was boiled at 85° C. for one hour with a solution of distilled water mixed with a 37% hydrochloric acid in a boiling apparatus. The boiled solid portion was thereafter washed 2 times with deionized water.

The solid portion was pressed in a screw press for partial removal of liquids therefrom.

The resulting cellulosic feedstock was thereafter ground in a stone grinder to a particle length of less than one millimeter.

The nitrogen and protein containing compounds were removed by pH Gradient Electrophoresis employing a 10% hydrogen chloride wash.

The resulting portion was partially dried by a drum dryer wherein 80% of the liquids were dried.

The partially dried portion was pressed by a screw press and thereafter packed in a pellet machine.

Experimental Results:

As seen in FIG. 5, a resulting combustion product composition was produced in the system described hereinabove wherein the combustion product composition generally comprises 11% oil, 65% cellulose, 10% hemicellulose, 2% lignin, 5% protein containing organic compound, 3% nitrogen containing organic compound, 1% minerals, 2% sand and 1% dirt. The caloric value of the resulting combustion product is approximately 9000 BTU/Pound.

Example 4

Figure 6:
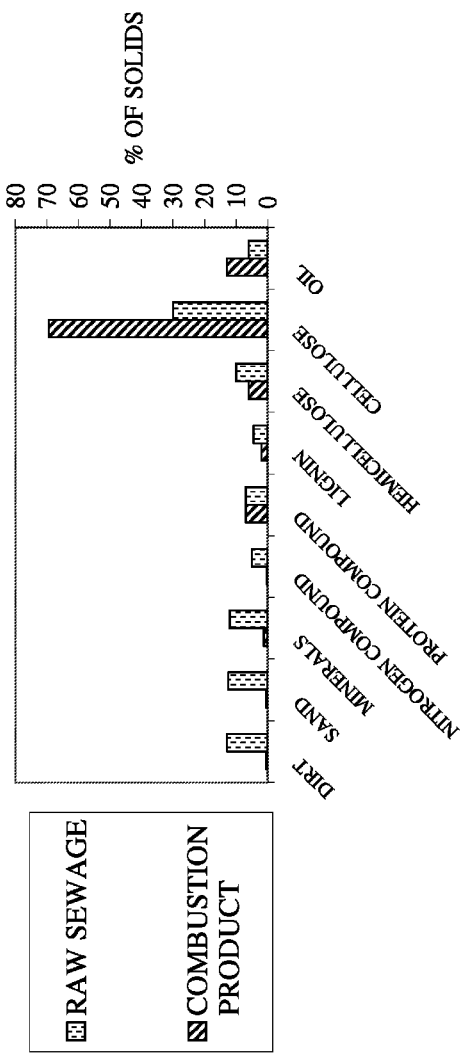
FIG. 6 is a graph of an additional solid composition obtained from raw sewage Vs. a cellulosic product composition processed in the systems of FIG. 1 and FIG. 4.

Experimental Procedure 120 m$^3$ of raw sewage, including a solid portion of approximately 0.05% of the raw sewage, was obtained from a municipal sewage waste system. As seen in FIG. 6, the composition of the raw sewage solid portion generally comprises 6% oil, 30% cellulose, 10% hemicellulose, 4.5% lignin, 7% protein containing organic compound, 5% nitrogen containing organic compound, 12.1% minerals, 12.5% sand and 12.9% dirt.

The raw sewage was introduced into a hydrocyclone centrifuge at a pressure of 3 Atm for initial sand and dirt removal from the raw sewage.

Thereafter the raw sewage was introduced into a vibration separator commercially available from the Sewco company of 8029 US Highway 25 Florence, Ky., USA under catalogue model SS of Sanitary Separators for entrapping solids therein by use of vibration. The residual liquid portion was discarded.

Secondary sand removal was performed by sedimentation in a conical-shaped pool wherein the sand sunk to the bottom of the pool. The sedimented sand was discarded.

The solid portion was pasteurized in a pasteurization device at a temperature of 72° C. for two minutes for partial sterilization thereof.

Mineral removal was performed by use of a chemical wash wherein the solid portion was washed with a solution of distilled water mixed with a 2% hydrochloric acid. The solid portion was thereafter washed with soft water.

The solid portion was pressed in a screw press for partial removal of liquids therefrom.

The resultant cellulosic feedstock was ground in a ball grinder to 100 microns. The ground cellulosic feedstock was pressed in a screw press, dried in a greenhouse for 4 days and thereafter packed in a pellet machine.

Experimental Results:

As seen in FIG. 6, a resulting combustion product composition was produced in the system described hereinabove wherein the combustion product composition generally comprises 13% oil, 69.4% cellulose, 6% hemicellulose, 2% lignin, 7% protein containing organic compound, 0.3% nitrogen containing organic compound, 1.3% minerals, 0.5% sand and 0.5% dirt. The caloric value of the resulting combustion product is approximately 9000 BTU/Pound.

Figure 7:
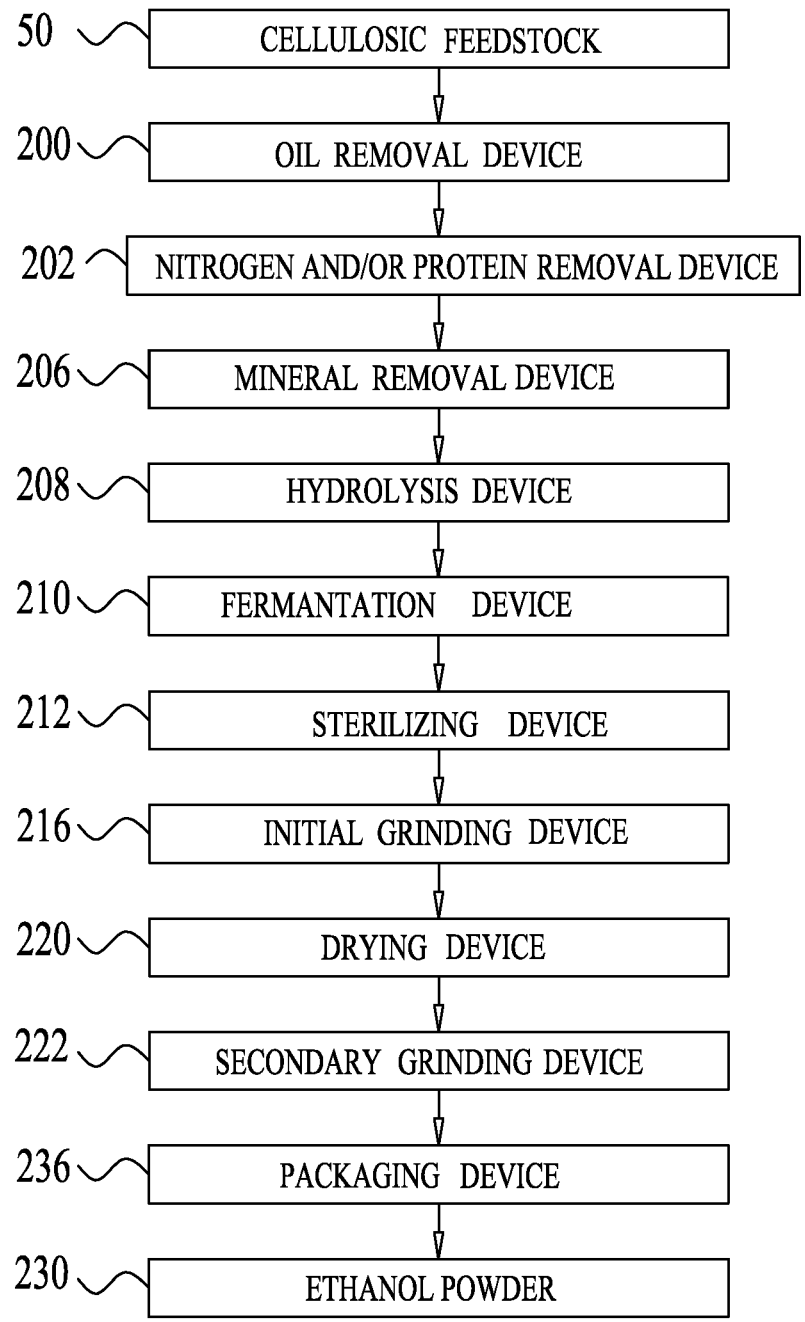
FIG. 7 is a simplified block diagram of a system for manufacturing a cellulosic product from cellulosic feedstock, constructed and operative in accordance with another embodiment of the present invention.

Reference is now made to FIG. 7, which is a simplified block diagram of a system for manufacturing ethanol powder from cellulosic feedstock, constructed and operative in accordance with an embodiment of the present invention.

As seen in FIG. 7, the cellulosic feedstock 50 may be introduced into an oil removal device 200 for removal of oil therefrom in any suitable manner, such as by an oil filter which may comprise a chemical filter, such as a silica containing filter, a biological filter, such as a cellulose containing filter, a device employing DAF, a conveyor belt, such as a belt formed of conveyor belt mesh, a centrifuge, a flow centrifuge, a filter press, a screw press, a disk filter, a media filter, such as a media filter comprising fibers, nettings, a filter employing backflushing technology. The chemical filter may include chemical washes, such as an hexane ($CH_3(CH_2)_4CH_3$) wash, which is operative to be dissipated along with oil adsorbed thereto.

The cellulosic feedstock 50 may be introduced into a nitrogen and/or protein removal device 202 for removal of the nitrogen and protein containing compounds by any suitable means. Nitrogen and/or protein removal device 202 may be formed of any one of the abovementioned apparati forming nitrogen and/or protein removal device 104 of FIG. 4.

The cellulosic feedstock 50 may be introduced into a secondary mineral removal device 206 for further removal of minerals within cellulosic feedstock 50 by any suitable means. Secondary mineral removal device 206 may be formed of any one of the abovementioned apparati forming mineral removal device 42 of FIG. 1.

The cellulosic feedstock 50 may be introduced into any suitable hydrolysis device 208 for hydrolyzing cellulosic feedstock 50. Hydrolysis device may employ any suitable means for hydrolyzing the cellulosic feedstock 50, such as by acid hydrolysis, enzymatic hydrolysis or thermochemical hydrolysis.

Thereafter the hydrolyzed cellulosic feedstock 50 may be introduced into any suitable fermentation device 210 so as to ferment the hydrolyzed cellulosic feedstock 50 by any suitable means, such as by use of yeast or growth of yeast.

The cellulosic feedstock 50 may be introduced into a sterilizing device 212 for sterilizing cellulosic feedstock 50 by any suitable means. Sterilizing device 212 may be formed of any one of the abovementioned apparati forming sterilizing device 40 of FIG. 1. Alternatively, the cellulosic feedstock 50 may be partially sterilized, such as by being introduced into a pasteurization device for pasteurizing the cellulosic feedstock 50.

The cellulosic feedstock 50 may be ground in an initial grinding device 216 by any suitable means. Grinding device 216 may be formed of any one of the above-mentioned apparati forming grinding device 102 of FIG. 4.

The cellulosic feedstock 50 may be introduced into a drying device 220 for at least partial drying of cellulosic feedstock 50 by any suitable means. Drying device 220 may be formed of any one of the abovementioned apparati forming drying device 110 of FIG. 4.

The cellulosic feedstock 50 may be ground again in a secondary grinding device 222 by any suitable means. Grinding device 222 may be formed of any one of the abovementioned apparati forming grinding device 102 of FIG. 4. The cellulosic feedstock 50 may be ground to any suitable particle size, such as to particles with a size of approximately less than 500 microns so as to form a powder therefrom.

A resulting ethanol powder 230 may be thereafter packaged in a packaging device 236 by any suitable means, such as by employing vacuum packing or pellet packing in a pellet machine, for example.

It is appreciated that the order of using the devices described hereinabove may be alternated so as to produce ethanol powder 230 from cellulosic feedstock 50.

A skilled artisan will appreciate that in the process of producing ethanol powder 230 some of the devices described hereinabove may be obviated without compromising the quality of the produced ethanol powder 230.

The resulting ethanol powder 230 is obtained from the system described hereinabove. The ethanol powder 230 is a composition substantially comprising an oil content of 1-10% thereof; a cellulose content of 50-99% thereof; a hemicellulose content of 2-20% thereof; a lignin content of less than 12% thereof; a nitrogen containing organic compound content of up to 15% thereof; a protein containing organic compound content of up to 15% thereof; a sand content of less than 5% thereof a mineral content of less than 5% thereof and a dirt content of less than 5% thereof.

It is noted that the oil content may be an oil content of 1% thereof, an oil content of 1-2% thereof, an oil content of 1-3% thereof, an oil content of 1-4% thereof, an oil content 1-5% thereof, an oil content of 1-6% thereof, an oil content of 1-7% thereof, an oil content of 1-8% thereof, an oil content of 1-9% thereof or an oil content of 10% thereof.

The cellulose content may be a cellulose content of 50-55% thereof, a cellulose content of 55-60% thereof, a cellulose content of 60-65% thereof, a cellulose content of 65-70% thereof, a cellulose content of 70-75% thereof, a cellulose content of 75-80% thereof, a cellulose content of 80-85% thereof, a cellulose content of 85-90% thereof, a cellulose content of 90-95% thereof or a cellulose content of 95-99% thereof.

The hemicellulose content may be a hemicellulose content of 2% thereof, a hemicellulose content of 2-3% thereof, a hemicellulose content of 2-4% thereof, a hemicellulose content of 2-5% thereof; a hemicellulose content of 2-6% thereof, a hemicellulose content of 2-7% thereof, a hemicellulose content of 2-8% thereof, a hemicellulose content of 2-9% thereof, a hemicellulose content of 2-10% thereof, a hemicellulose content of 2-11% thereof, a hemicellulose content of 2-12% thereof, a hemicellulose content of 2-13% thereof, a hemicellulose content of 2-14% thereof, a hemicellulose content of 2-15% thereof, a hemicellulose content of 2-16% thereof, a hemicellulose content of 2-17% thereof, a hemicellulose content of 2-18% thereof, a hemicellulose content of 2-19% thereof or a hemicellulose content of 20% thereof.

The lignin content may be a lignin content of less than 12% thereof, a lignin content of less than 11% thereof, a lignin content of less than 10% thereof, a lignin content of less than 9% thereof, a lignin content of less than 8% thereof, a lignin content of less than 7% thereof, a lignin content of less than 6% thereof, a lignin content of less than 5% thereof, a lignin content of less than 4% thereof, a lignin content of less than 3% thereof, a lignin content of less than 2% thereof or a lignin content of less than 1% thereof.

The nitrogen containing organic compound content may be a content of up to 1% thereof, a nitrogen containing organic compound content of up to 2% thereof, a nitrogen containing organic compound content of up to 3% thereof, a nitrogen containing organic compound content of up to 4% thereof, a nitrogen containing organic compound content of up to 5% thereof, a nitrogen containing organic compound content of up to 6% thereof, a nitrogen containing organic compound content of up to 7% thereof, a nitrogen containing organic compound content of up to 8% thereof, a nitrogen containing organic compound content of up to 9% thereof, a nitrogen containing organic compound content of up to 10% thereof, a nitrogen containing organic compound content of up to 11% thereof, a nitrogen containing organic compound content of up to 12% thereof, a nitrogen containing organic compound content of up to 13% thereof, a nitrogen containing organic compound content of up to 14% thereof or a nitrogen containing organic compound content of up to 15% thereof.

The protein containing organic compound content may be a protein containing organic compound content of up to 1% thereof, a protein containing organic compound content of up to 2% thereof, a protein containing organic compound content of up to 3% thereof, a protein containing organic compound content of up to 4% thereof, a protein containing organic compound content of up to 5% thereof, a protein containing organic compound content of up to 6% thereof, a protein containing organic compound content of up to 7% thereof, a protein containing organic compound content of up to 8% thereof, a protein containing organic compound content of up to 9% thereof, a protein containing organic compound content of up to 10% thereof, a protein containing organic compound content of up to 11% thereof, a protein containing organic compound content of up to 12% thereof, a protein containing organic compound content of up to 13% thereof, a protein containing organic compound content of up to 14% thereof or a protein containing organic compound content of up to 15% thereof.

The sand content may be less than 5% thereof, less than 4% thereof, less than 3% thereof, less than 2% thereof, less than 1% thereof or less than 0.5% thereof. The mineral content may be less than 5% thereof, less than 4% thereof, less than 3% thereof, less than 2% thereof, less than 1% thereof or less than 0.5% thereof. The dirt content may be less than 5% thereof, less than 4% thereof, less than 3% thereof, less than 2% thereof, less than 1% thereof or less than 0.5% thereof.

The ethanol powder 230 may comprise particles with a size of 0.01 microns-100 mm, a size of 0.01-1 microns, a size of 1-5 microns, a size of 5-10 microns, a size of 10-20 microns, a size of 20-30 microns, a size of 30-40 microns, a size of 40-50 microns, a size of 50-60 microns, a size of 60-70 microns, a size of 70-80 microns, a size of 80-90 microns, a size of 90-100 microns, a size of 100-150 microns, a size of 150-200 microns, a size of 200-250 microns, a size of 250-300 microns, a size of 300-350 microns, a size of 350-400 microns, a size of 400-450 microns, a size of 450-500 microns, a size of 500-550 microns, a size of 550-600 microns, a size of 600-650 microns, a size of 650-700 microns, a size of 750-800 microns, a size of 800-850 microns, a size of 850-900 microns, a size of 900-950 microns, a size of 950-1000 microns, a size of 1-5 mm, a size of 5-10 mm, a size of 10-15 mm, a size of 15-20 mm, a size of 20-25 mm, a size of 25-30 mm, a size of 30-35 mm, a size of 35-40 mm, a size of 40-45 mm, a size of 45-50 mm, a size of 50-55 mm, a size of 55-60 mm, a size of 60-65 mm, a size of 65-70 mm, a size of 70-75 mm, a size of 75-80 mm, a size of 80-85 mm, a size of 85-90 mm, a size of 90-95 mm or a size of 95-100 mm.

The caloric value of the ethanol powder 230 may be in the range of 5000-16000 BTU/Pound. It is noted that the caloric value of the ethanol powder 230 may be in the range of 5000-6000 BTU/Pound; in the range of 6000-7000 BTU/Pound; in the range of 7000-8000 BTU/Pound; in the range of 8000-9000 BTU/Pound; in the range of 9000-10000 BTU/Pound; in the range of 10000-11000 BTU/Pound; in the range of 11000-12000 BTU/Pound; in the range of 12000-13000 BTU/Pound; in the range of 13000-14000 BTU/Pound; in the range of 14000-15000 BTU/Pound or in the range of 15000-16000 BTU/Pound.

It is noted that the ethanol may not be ground to powder but rather remain in a fibrous form. Additionally, any form of an ethanol-containing product may be produced in the system described hereinabove. For example, liquid ethanol may be produced within the system described hereinabove.

Examples 5 and 6 describe producing ethanol powder 230 from sewage 10 in the system described in reference to FIGS. 1 and 7.

Example 5

Figure 8:
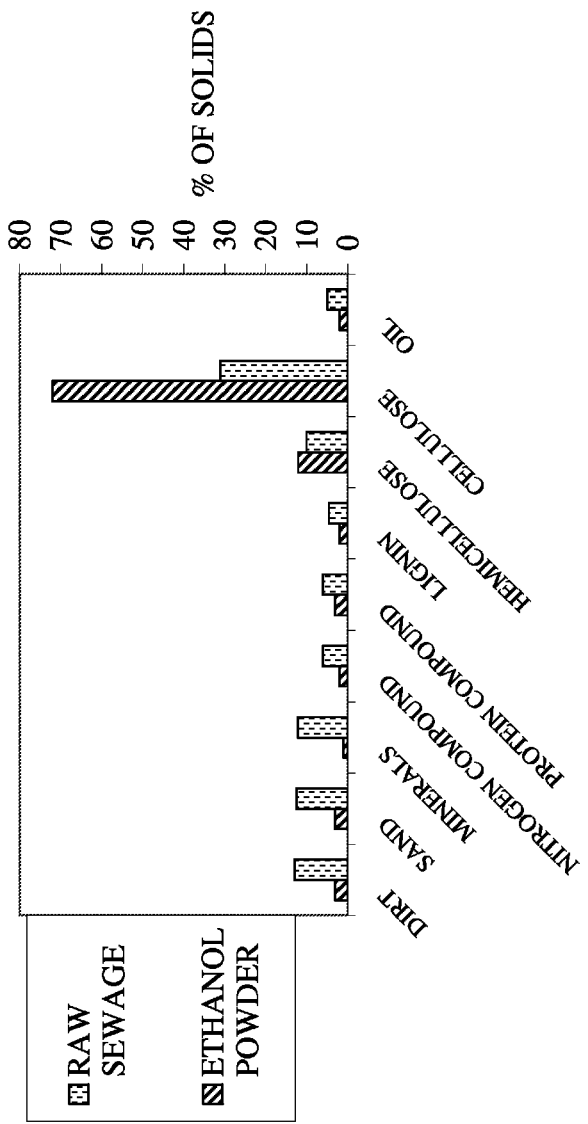
FIG. 8 is a graph of a solid composition obtained from raw sewage Vs. a cellulosic product composition processed in the systems of FIG. 1 and FIG. 7.

Experimental Procedure 100 m$^3$ of raw sewage, including a solid portion of approximately 0.1% of the raw sewage, was obtained from a municipal sewage waste system. As seen in FIG. 8, the composition of the raw sewage solid portion generally comprises 5% oil, 31% cellulose, 10% hemicellulose, 4.5% lignin, 6% protein containing organic compound, 6% nitrogen containing organic compound, 12.1% minerals, 12.5% sand and 12.9% dirt.

The raw sewage was introduced into a hydrocyclone centrifuge at a pressure of 3 Atm for initial sand removal from the raw sewage.

Thereafter the raw sewage was introduced into an entrapping device formed of a net of a 250 micron mesh. Approximately 50 Kg of solids were entrapped within the net. The residual liquid portion was discarded.

Secondary sand removal was performed by sedimentation in a conical-shaped pool wherein the sand sunk to the bottom of the pool. The sedimented sand was discarded.

Dirt removal was performed thereafter in a hydrocyclone centrifuge at a pressure of 3 Atm. The remaining portion was introduced into a magnet containing device wherein a portion of iron was magnetically removed.

The solid portion was introduced into a sterilizer at a temperature of 85° C. for 10 minutes.

Mineral removal was performed by use of a chemical wash wherein the solid portion was boiled at 85° C. for one hour with a solution of distilled water mixed with a 37% hydrochloric acid in a boiling apparatus. The boiled solid portion was thereafter washed 2 times with deionized water.

The solid portion was pressed in a screw press for partial removal of liquids therefrom.

Oil was removed from the resultant cellulosic feedstock by washing the resulting portion with a 1% hexane containing wash. Thereafter the solid portion and hexane containing wash mixture was heated to 80° C. for dissipating the hexane containing wash along with a portion of the oil.

A portion of the nitrogen and protein containing compounds were removed from the cellulosic feedstock by pH Gradient Electrophoresis employing a 10% hydrogen chloride wash.

An enzyme, commercially available from the Genencor Division of Danisco US Inc. of 200 Meridian Centre Blvd. Rochester, N.Y., USA under the name ACCELLERASE® was added to the cellulosic feedstock at a concentration of 5 milliliters per milligram. A buffer of 50 miliMole of sodium acetate with a 5.0 pH was added. The mixture was autoclaved, incubated at 50° C. with shaking at 125 rpm for 10 hours.

Thereafter the hydrolyzed cellulosic feedstock was fermented by incubating the hydrolyzed cellulosic feedstock in screw-cup anaerobic tubes at 30° C. with a yeast starter of *Saccharomyces cerevisiae* Y103.

The cellulosic feedstock was thereafter ground in a stone grinder.

The solid portion was partially dried in a drum dryer wherein 80% of the liquids were dried.

The partially dried portion was ground in a ball grinder to a powder with a particle length of less than 500 microns.

The powder was thereafter packed.

Experimental Results:

As seen in FIG. 8, a resulting ethanol powder composition was produced in the system described hereinabove wherein the ethanol powder composition generally comprises 2% oil, 72% cellulose, 12% hemicellulose, 2% lignin, 3% protein containing organic compound, 2% nitrogen containing organic compound, 1% minerals, 3% sand and 3% dirt. The caloric value of the resulting ethanol powder is approximately 6000 BTU/Pound. The average particle diameter of the ethanol powder is less than 100 microns, approximately.

Example 6

Figure 9:
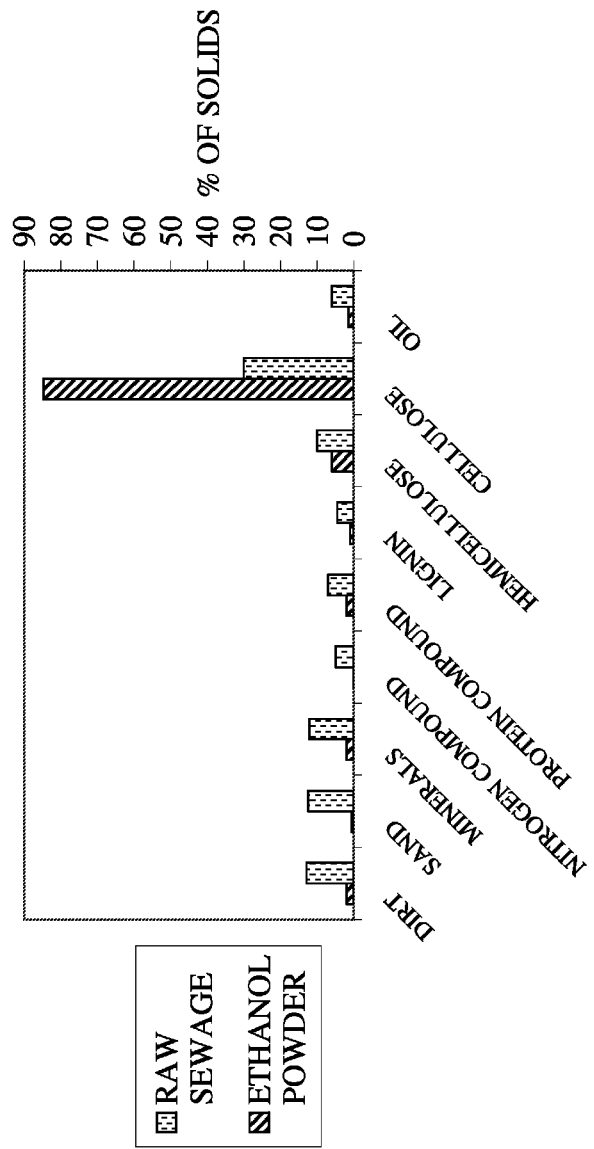
FIG. 9 is a graph of an additional solid composition obtained from raw sewage Vs. a cellulosic product composition processed in the systems of FIG. 1 and FIG. 7.

Experimental Procedure 120 m³ of raw sewage, including a solid portion of approximately 0.05% of the raw sewage, was obtained from a municipal sewage waste system. As seen in FIG. 9, the composition of the raw sewage solid portion generally comprises 6% oil, 30% cellulose, 10% hemicellulose, 4.5% lignin, 7% protein containing organic compound, 5% nitrogen containing organic compound, 12.1% minerals, 12.5% sand and 12.9% dirt.

The raw sewage was introduced into a hydrocyclone centrifuge at a pressure of 3 Atm for initial sand and dirt removal from the raw sewage.

Thereafter the raw sewage was introduced into a vibration separator commercially available from the Sewco company of 8029 US Highway 25 Florence, Ky., USA under catalogue model SS of Sanitary Separators for entrapping solids therein by use of vibration. The residual liquid portion was discarded.

Secondary sand removal was performed by sedimentation in a conical-shaped pool wherein the sand sunk to the bottom of the pool. The sedimented sand was discarded.

The solid portion was pasteurized in a pasteurization device at a temperature of 72° C. for two minutes for partial sterilization thereof.

Mineral removal was performed by use of a chemical wash wherein the solid portion was washed with a solution of distilled water mixed with a 2% hydrochloric acid. The solid portion was thereafter washed with soft water.

The solid portion was pressed in a screw press for partial removal of liquids therefrom.

Oil was removed from the resultant cellulosic feedstock by washing the resulting portion with a 1% hexane containing wash. Thereafter the solid portion and hexane containing wash mixture was heated to 80° C. for dissipating the hexane containing wash along with a portion of the oil.

An enzyme, commercially available from the Genencor Division of Danisco US Inc. of 200 Meridian Centre Blvd. Rochester, N.Y., USA under the name ACCELLERASE® was added to the cellulosic feedstock at a concentration of 5 milliliters per milligram. A buffer of 50 miliMole of sodium acetate with a 5.0 pH was added. The mixture was autoclaved, incubated at 50° C. with shaking at 125 rpm.

Thereafter the hydrolyzed cellulosic feedstock was fermented by incubating the hydrolyzed cellulosic feedstock in screw-cup anaerobic tubes at 30° C. with a yeast starter of *Saccharomyces cerevisiae* Y103.

The cellulosic feedstock was dried in an oven at 105° C. and thereafter ground to 100 microns in a stone grinder.

Experimental Results:

As seen in FIG. 9, a resulting ethanol powder composition was produced in the system described hereinabove wherein the ethanol powder composition generally comprises 1.5% oil, 84.4% cellulose, 6% hemicellulose, 1% lignin, 2% protein containing organic compound, 0.2% nitrogen containing organic compound, 2% minerals, 0.5% sand and 2% dirt. The caloric value of the resulting ethanol powder is approximately 6000 BTU/Pound. The average particle diameter of the ethanol powder is 100 microns, approximately.

Figure 10:
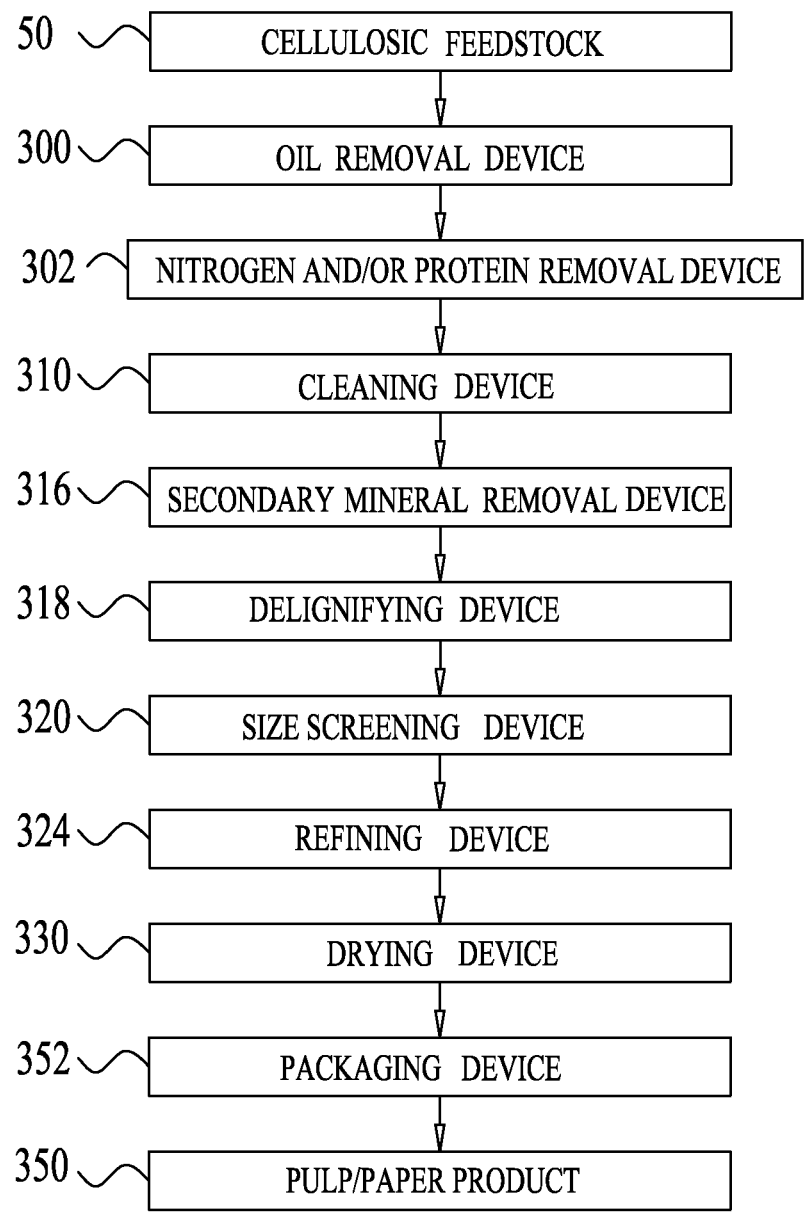
FIG. 10 is a simplified block diagram of a system for manufacturing a cellulosic product from cellulosic feedstock, constructed and operative in accordance with yet another embodiment of the present invention.

Reference is now made to FIG. 10, which is a simplified block diagram of a system for manufacturing a pulp or paper product from cellulosic feedstock, constructed and operative in accordance with an embodiment of the present invention. As seen in FIG. 10, the cellulosic feedstock 50 may be introduced into an oil removal device 300 for removal of oil therefrom in any suitable manner. Oil removal device 300 may be formed of any one of the abovementioned apparati forming oil removal device 200 of FIG. 7.

The cellulosic feedstock 50 may be introduced into a nitrogen and/or protein removal device 302 for removal of the nitrogen and protein containing compounds by any suitable means. Nitrogen and/or protein removal device 302 may be formed of any one of the abovementioned apparati forming nitrogen and/or protein removal device 104 of FIG. 4.

The cellulosic feedstock may be introduced into a cleaning device 310, such as a cleaning device employing a hydrolyser or any other suitable means.

The cellulosic feedstock 50 may be introduced into a secondary mineral removal device 316 for further removal of minerals within cellulosic feedstock 50 by any suitable means. Secondary mineral removal device 316 may be formed of any one of the abovementioned apparati forming mineral removal device 42 of FIG. 1.

The cellulosic feedstock 50 may be introduced into a delignifying device 318 for removing a portion of the lignin content from cellulosic feedstock 50. Delignifying device 318 may employ any suitable method for delignifying the cellulosic feedstock 50, such as chemical delignification using oxygen, ozone or a proxy, for example.

The particles of the cellulosic feedstock 50 may be separated according to size in a size screening device 320 by any suitable means, such as by use of nettings with different mesh sizes. The cellulosic feedstock 50 may be separated into a plurality of sizes. For example, the cellulosic feedstock 50 may be introduced into nettings operative to trap cellulosic feedstock with a particle size of at least 400 microns or cellulosic feedstock 50 with a particle size in the range of 300-400 microns or cellulosic feedstock 50 with a particle size in the range of 200-300 microns or cellulosic feedstock 50 with a particle size in the range of 100-200 microns or cellulosic feedstock 50 with a particle size less than 100 microns. The cellulosic feedstock 50 is separated according to size so as to be used to produce a variety of products. For example, the cellulosic feedstock 50 with a particle size of at least 400 microns is used to produce newspaper and the cellulosic feedstock 50 with a particle size in the range of 100-400 microns is used to produce gray paper.

The cellulosic feedstock 50 may be introduced into a refining device 324 for enlarging a surface area of the cellulosic feedstock fiber, typically by applying pressure thereon by any suitable means. Enlarging the surface area of the fibers allows for improved adherence of the fibers to each other so as to produce a paper or pulp product therefrom.

The cellulosic feedstock 50 may be introduced into a drying device 330 for at least partial drying of cellulosic feedstock 50 by any suitable means. Drying device 330 may be formed of any one of the abovementioned apparati forming drying device 110 of FIG. 4.

A resultant pulp or paper product 350 may be thereafter packaged in a packaging device 352 by any suitable means, such as by employing vacuum packing, for example. It is appreciated that packaging device 352 may be obviated.

It is appreciated that the order of using the devices described hereinabove may be alternated so as to produce the pulp or paper product 350 from cellulosic feedstock 50.

A skilled artisan will appreciate that in the process of producing the pulp or paper product 350 some of the devices described hereinabove may be obviated without compromising the quality of the produced pulp or paper product 350.

The resulting pulp or paper product 350 is obtained from the system described hereinabove. The pulp or paper product 350 is a composition substantially comprising an oil content of 1-10% thereof a cellulose content of 50-90% thereof; a hemicellulose content of 2-20% thereof; a lignin content of less than 4% thereof; a nitrogen containing organic compound content of up to 15% thereof; a protein containing organic compound content of up to 15% thereof; a sand content of less than 5% thereof; a mineral content of less than 5% thereof and a dirt content of less than 5% thereof.

It is noted that the oil content may be an oil content of 1% thereof, an oil content of 1-2% thereof, an oil content of 1-3% thereof, an oil content of 1-4% thereof, an oil content 1-5% thereof, an oil content of 1-6% thereof, an oil content of 1-7% thereof, an oil content of 1-8% thereof, an oil content of 1-9% thereof or an oil content of 10% thereof.

The cellulose content may be a cellulose content of 50-55% thereof, a cellulose content of 55-60% thereof, a cellulose content of 60-65% thereof, a cellulose content of 65-70% thereof, a cellulose content of 70-75% thereof, a cellulose content of 75-80% thereof, a cellulose content of 80-85% thereof or a cellulose content of 85-90% thereof.

The hemicellulose content may be a hemicellulose content of 2% thereof, a hemicellulose content of 2-3% thereof, a hemicellulose content of 2-4% thereof, a hemicellulose content of 2-5% thereof; a hemicellulose content of 2-6% thereof, a hemicellulose content of 2-7% thereof, a hemicellulose content of 2-8% thereof, a hemicellulose content of 2-9% thereof, a hemicellulose content of 2-10% thereof, a hemicellulose content of 2-11% thereof, a hemicellulose content of 2-12% thereof, a hemicellulose content of 2-13% thereof, a hemicellulose content of 2-14% thereof, a hemicellulose content of 2-15% thereof, a hemicellulose content of 2-16% thereof, a hemicellulose content of 2-17% thereof, a hemicellulose content of 2-18% thereof, a hemicellulose content of 2-19% thereof or a hemicellulose content of 20% thereof.

The lignin content may be a lignin content of less 4% thereof, a lignin content of less than 3% thereof, a lignin content of less than 2% thereof or a lignin content of less than 1% thereof.

The nitrogen containing organic compound content may be a content of up to 1% thereof, a nitrogen containing organic compound content of up to 2% thereof, a nitrogen containing organic compound content of up to 3% thereof, a nitrogen containing organic compound content of up to 4% thereof, a nitrogen containing organic compound content of up to 5% thereof, a nitrogen containing organic compound content of up to 6% thereof, a nitrogen containing organic compound content of up to 7% thereof, a nitrogen containing organic compound content of up to 8% thereof, a nitrogen containing organic compound content of up to 9% thereof, a nitrogen containing organic compound content of up to 10% thereof, a nitrogen containing organic compound content of up to 11% thereof, a nitrogen containing organic compound content of up to 12% thereof, a nitrogen containing organic compound content of up to 13% thereof, a nitrogen containing organic compound content of up to 14% thereof or a nitrogen containing organic compound content of up to 15% thereof.

The protein containing organic compound content may be a content of up to 1% thereof, a protein containing organic compound content of up to 2% thereof, a protein containing organic compound content of up to 3% thereof, a protein containing organic compound content of up to 4% thereof, a protein containing organic compound content of up to 5% thereof, a protein containing organic compound content of up to 6% thereof, a protein containing organic compound content of up to 7% thereof, a protein containing organic compound content of up to 8% thereof, a protein containing organic compound content of up to 9% thereof, a protein containing organic compound content of up to 10% thereof, a protein containing organic compound content of up to 11% thereof, a protein containing organic compound content of up to 12% thereof, a protein containing organic compound content of up to 13% thereof, a protein containing organic compound content of up to 14% thereof or a protein containing organic compound content of up to 15% thereof.

The sand content may be less than 5% thereof, less than 4% thereof, less than 3% thereof, less than 2% thereof, less than 1% thereof or less than 0.5% thereof. The mineral content may be less than 5% thereof, less than 4% thereof, less than 3% thereof, less than 2% thereof, less than 1% thereof or less than 0.5% thereof. The dirt content may be less than 5% thereof, less than 4% thereof, less than 3% thereof, less than 2% thereof, less than 1% thereof or less than 0.5% thereof.

The pulp or paper product 350 may comprise particles with a size of 0.01 microns-100 mm, a size of 0.01-1 microns, a size of 1-5 microns, a size of 5-10 microns, a size of 10-20 microns, a size of 20-30 microns, a size of 30-40 microns, a size of 40-50 microns, a size of 50-60 microns, a size of 60-70 microns, a size of 70-80 microns, a size of 80-90 microns, a size of 90-100 microns, a size of 100-150 microns, a size of 150-200 microns, a size of 200-250 microns, a size of 250-300 microns, a size of 300-350 microns, a size of 350-400 microns, a size of 400-450 microns, a size of 450-500 microns, a size of 500-550 microns, a size of 550-600 microns, a size of 600-650 microns, a size of 650-700 microns, a size of 750-800 microns, a size of 800-850 microns, a size of 850-900 microns, a size of 900-950 microns, a size of 950-1000 microns, a size of 1-5 mm, a size of 5-10 mm, a size of 10-15 mm, a size of 15-20 mm, a size of 20-25 mm, a size of 25-30 mm, a size of 30-35 mm, a size of 35-40 mm, a size of 40-45 mm, a size of 45-50 mm, a size of 50-55 mm, a size of 55-60 mm, a size of 60-65 mm, a size of 65-70 mm, a size of 70-75 mm, a size of 75-80 mm, a size of 80-85 mm, a size of 85-90 mm, a size of 90-95 mm or a size of 95-100 mm.

Examples 7 and 8 describe producing a pulp or paper product 350 from sewage 10 in the system described in reference to FIGS. 1 and 10.

Example 7

Figure 11:
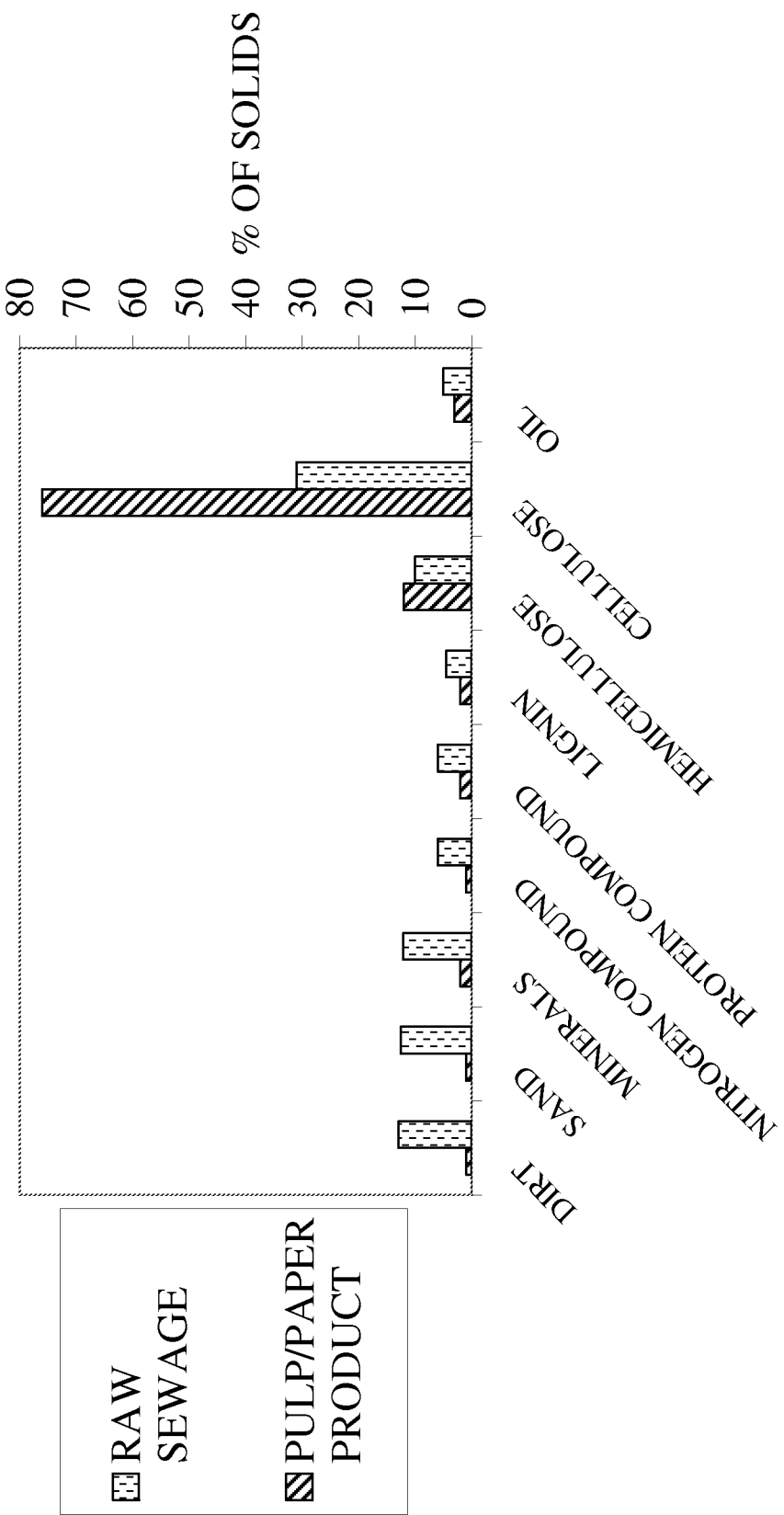
FIG. 11 is a graph of a solid composition obtained from raw sewage Vs. a cellulosic product composition processed in the systems of FIG. 1 and FIG. 10;\

Experimental Procedure 100 m³ of raw sewage, including a solid portion of approximately 0.1% of the raw sewage, was obtained from a municipal sewage waste system. As seen in FIG. 11, the composition of the raw sewage solid portion generally comprises 5% oil, 31% cellulose, 10% hemicellulose, 4.5% lignin, 6% protein containing organic compound, 6% nitrogen containing organic compound, 12.1% minerals, 12.5% sand and 12.9% dirt.

The raw sewage was introduced into a hydrocyclone centrifuge at a pressure of 3 Atm for initial sand removal from the raw sewage.

Thereafter the raw sewage was introduced into an entrapping device formed of a net of a 250 micron mesh. Approximately 50 Kg of solids were entrapped within the net. The residual liquid portion was discarded.

Secondary sand removal was performed by sedimentation in a conical-shaped pool wherein the sand sunk to the bottom of the pool. The sedimented sand was discarded.

Dirt removal was performed thereafter in a hydrocyclone centrifuge at a pressure of 3 Atm. The remaining portion was introduced into a magnet containing device wherein a portion of iron was magnetically removed.

The solid portion was introduced into a sterilizer at a temperature of 85° C. for 10 minutes.

Mineral removal was performed by use of a chemical wash wherein the solid portion was boiled at 85° C. for one hour with a solution of distilled water mixed with a 37% hydrochloric acid in a boiling apparatus. The boiled solid portion was thereafter washed 2 times with deionized water.

The solid portion was pressed in a screw press for partial removal of liquids therefrom.

Oil was removed from the resultant cellulosic feedstock by washing the resulting portion with a 1% hexane containing wash. Thereafter the solid portion and hexane containing wash mixture was heated to 80° C. for dissipating the hexane containing wash along with a portion of the oil.

The nitrogen and protein containing compounds were removed from the cellulosic feedstock by pH Gradient Electrophoresis employing a 10% hydrogen chloride wash.

The cellulosic feedstock was delignified in a delignifying device using active oxygen.

The delignified cellulosic feedstock was introduced into a netting of a 400 micron mesh and thereafter into a netting of a 100 micron mesh for size screening thereof.

The resulting screened fibers were partially dried in a drum dryer wherein 80% of the liquids were dried.

The dried resulting fibers were thereafter packed by size to be formed into paper or may be used as pulp.

Experimental Results:

As seen in FIG. 11, a resulting pulp or paper product composition was produced in the system described hereinabove wherein the pulp or paper product composition generally comprises 3% oil, 76% cellulose, 12% hemicellulose, 2% lignin, 2% protein containing organic compound, 1% nitrogen containing organic compound, 2% minerals, 1% sand and 1% dirt. The diameter of the particles of the paper or pulp products was in the range of 50 microns-5 mm.

Example 8

Figure 12:
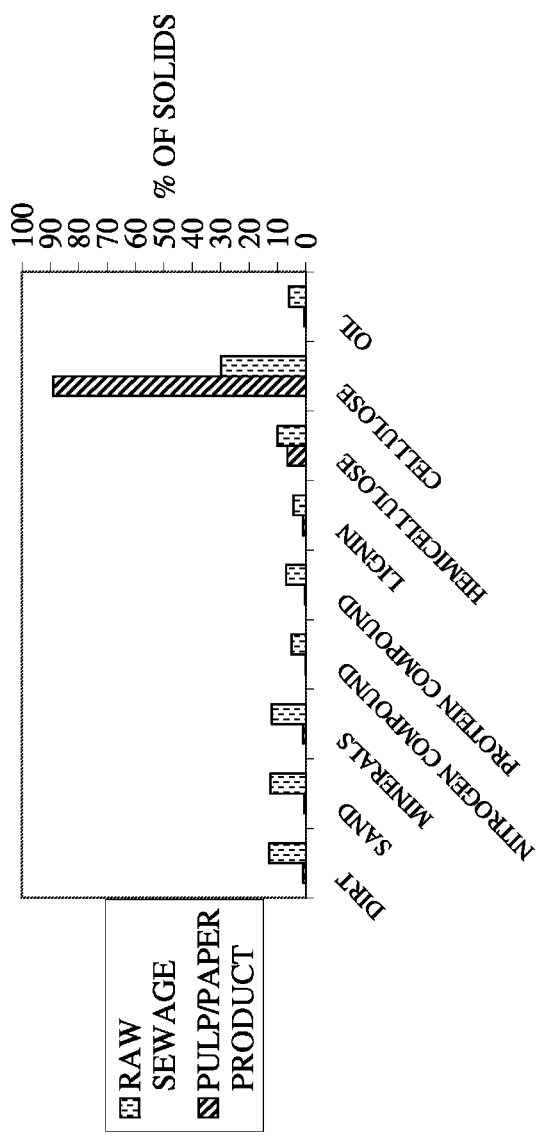
FIG. 12 is a graph of an additional solid composition obtained from raw sewage Vs. a cellulosic product composition processed in the systems of FIG. 1 and FIG. 10.

Experimental Procedure 120 m³ of raw sewage, including a solid portion of approximately 0.05% of the raw sewage, was obtained from a municipal sewage waste system. As seen in FIG. 12, the composition of the raw sewage solid portion generally comprises 6% oil, 30% cellulose, 10% hemicellulose, 4.5% lignin, 7% protein containing organic compound, 5% nitrogen containing organic compound, 12.1% minerals, 12.5% sand and 12.9% dirt.

The raw sewage was introduced into a hydrocyclone centrifuge at a pressure of 3 Atm for initial sand and dirt removal from the raw sewage.

Thereafter the raw sewage was introduced into a vibration separator commercially available from the Sewco company of 8029 US Highway 25 Florence, Ky., USA under catalogue model SS of Sanitary Separators for entrapping solids therein by use of vibration. The residual liquid portion was discarded.

Secondary sand removal was performed by sedimentation in a conical-shaped pool wherein the sand sunk to the bottom of the pool. The sedimented sand was discarded.

The solid portion was pasteurized in a pasteurization device at a temperature of 72° C. for two minutes for partial sterilization thereof.

Mineral removal was performed by use of a chemical wash wherein the solid portion was washed with a solution of distilled water mixed with a 2% hydrochloric acid. The solid portion was thereafter washed with soft water.

The solid portion was pressed in a screw press for partial removal of liquids therefrom.

Oil was removed from the resultant cellulosic feedstock by washing the resulting portion with a 1% hexane containing wash. Thereafter the resulting solid portion and wash mixture was heated to 80° C. for dissipating the hexane containing wash along with a portion of the oil.

Further mineral removal was performed by use of a chemical wash wherein the solid portion was washed with a solution of distilled water mixed with a 3% hydrochloric acid. The solid portion was thereafter washed with soft water.

The cellulosic feedstock was delignified in a delignifying device using ozone.

The delignified cellulosic feedstock was introduced into a netting of a 400 micron mesh and thereafter into a netting of a 100 micron mesh for size screening thereof.

The resulting screened fibers were partially dried in a drum dryer wherein 80% of the liquids were dried.

The dried resulting fibers were thereafter packed by size to be formed into paper or may be used as pulp.

Experimental Results:

As seen in FIG. 12, a resulting pulp or paper product was produced in the system described hereinabove wherein the pulp or paper product composition generally comprises 0.5% oil, 89% cellulose, 6.5% hemicellulose, 1% lignin, 0.3% protein containing organic compound, 0.2% nitrogen containing organic compound, 1% minerals, 0.5% sand and 1% dirt. The diameter of the particles of the paper or pulp products was in the range of 50 microns-5 mm.

Figure 13:
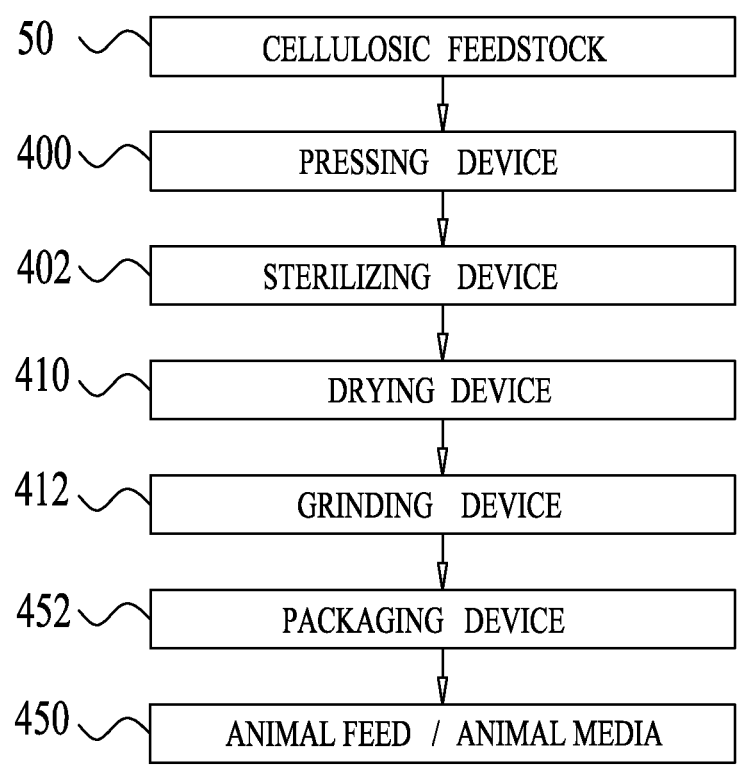
FIG. 13 is a simplified block diagram of a system for manufacturing a cellulosic product from cellulosic feedstock, constructed and operative in accordance with still another embodiment of the present invention.

Reference is now made to FIG. 13, which is a simplified block diagram of a system for manufacturing animal feed or animal media from cellulosic feedstock, constructed and operative in accordance with an embodiment of the present invention. As seen in FIG. 13, the cellulosic feedstock 50 may be pressed in a pressing device 400 by any suitable means. Pressing device 400 may be formed of any one of the abovementioned apparati forming pressing device 108 of FIG. 4.

The cellulosic feedstock 50 may be introduced into a sterilizing device 402 for sterilizing cellulosic feedstock 50 by any suitable means. Sterilizing device 402 may be formed of any one of the abovementioned apparati forming sterilizing device 40 of FIG. 1. Alternatively, the cellulosic feedstock 50 may be partially sterilized, such as by being introduced into a pasteurization device for pasteurizing the cellulosic feedstock 50.

The cellulosic feedstock 50 may be introduced into a drying device 410 for at least partial drying of cellulosic feedstock 50 by any suitable means. Drying device 410 may be formed of any one of the abovementioned apparati forming drying device 110 of FIG. 4.

The cellulosic feedstock 50 may be ground in a grinding device 412 by any suitable means. Grinding device 412 may be formed of any one of the above-mentioned apparati forming grinding device 102 of FIG. 4. The cellulosic feedstock 50 may be ground to any suitable particle size, such as to particles with a size of approximately less than 500 microns so as to form a powder therefrom.

A resulting animal feed or animal media 450 may be thereafter packaged in a packaging device 452 by any suitable means, such as by employing vacuum packing or pellet packing in a pellet machine, for example.

It is appreciated that the order of using the devices described hereinabove may be alternated so as to produce animal feed or animal media 450 from cellulosic feedstock 50.

A skilled artisan will appreciate that in the process of producing animal feed or animal media 450 some of the devices described hereinabove may be obviated without compromising the quality of the produced animal feed or animal media 450. It is noted that the term "animal media" refers to a substance placed on the floor of animal pens.

The resulting animal feed or animal media 450 is obtained from the system described hereinabove. The animal feed or animal medium 450 is a composition substantially comprising an oil content of 1-10% thereof; a cellulose content of 50-90% thereof; a hemicellulose content of 2-20% thereof; a lignin content of less than 12% thereof; a nitrogen containing organic compound content of up to 15% thereof; a protein containing organic compound content of up to 15% thereof; a sand content of less than 5% thereof; a mineral content of less than 5% thereof and a dirt content of less than 5% thereof.

It is noted that the oil content may be an oil content of 1% thereof, an oil content of 1-2% thereof, an oil content of 1-3% thereof, an oil content of 1-4% thereof, an oil content 1-5% thereof, an oil content of 1-6% thereof, an oil content of 1-7% thereof, an oil content of 1-8% thereof, an oil content of 1-9% thereof or an oil content of 10% thereof.

The cellulose content may be a cellulose content of 50-55% thereof, a cellulose content of 55-60% thereof, a cellulose content of 60-65% thereof, a cellulose content of 65-70% thereof, a cellulose content of 70-75% thereof, a cellulose content of 75-80% thereof, a cellulose content of 80-85% thereof or a cellulose content of 85-90% thereof.

The hemicellulose content may be a hemicellulose content of 2% thereof, a hemicellulose content of 2-3% thereof, a hemicellulose content of 2-4% thereof, a hemicellulose content of 2-5% thereof; a hemicellulose content of 2-6% thereof, a hemicellulose content of 2-7% thereof, a hemicellulose content of 2-8% thereof, a hemicellulose content of 2-9% thereof, a hemicellulose content of 2-10% thereof, a hemicellulose content of 2-11% thereof, a hemicellulose content of 2-12% thereof, a hemicellulose content of 2-13% thereof, a hemicellulose content of 2-14% thereof, a hemicellulose content of 2-15% thereof, a hemicellulose content of 2-16% thereof, a hemicellulose content of 2-17% thereof, a hemicellulose content of 2-18% thereof, a hemicellulose content of 2-19% thereof or a hemicellulose content of 20% thereof.

The lignin content may be a lignin content of less than 12% thereof, a lignin content of less than 11% thereof, a lignin content of less than 10% thereof, a lignin content of less than 9% thereof, a lignin content of less than 8% thereof, a lignin content of less than 7% thereof, a lignin content of less than 6% thereof, a lignin content of less than 5% thereof, a lignin content of less than 4% thereof, a lignin content of less than 3% thereof, a lignin content of less than 2% thereof or a lignin content of less than 1% thereof.

The nitrogen containing organic compound content may be a content of up to 1% thereof, a nitrogen containing organic compound content of up to 2% thereof, a nitrogen containing organic compound content of up to 3% thereof, a nitrogen containing organic compound content of up to 4% thereof, a nitrogen containing organic compound content of up to 5% thereof, a nitrogen containing organic compound content of up to 6% thereof, a nitrogen containing organic compound content of up to 7% thereof, a nitrogen containing organic compound content of up to 8% thereof, a nitrogen containing organic compound content of up to 9% thereof, a nitrogen containing organic compound content of up to 10% thereof, a nitrogen containing organic compound content of up to 11% thereof, a nitrogen containing organic compound content of up to 12% thereof, a nitrogen containing organic compound content of up to 13% thereof, a nitrogen containing organic compound content of up to 14% thereof or a nitrogen containing organic compound content of up to 15% thereof.

The protein containing organic compound content may be a content of up to 1% thereof, a protein containing organic compound content of up to 2% thereof, a protein containing organic compound content of up to 3% thereof, a protein containing organic compound content of up to 4% thereof, a protein containing organic compound content of up to 5% thereof, a protein containing organic compound content of up to 6% thereof, a protein containing organic compound content of up to 7% thereof, a protein containing organic compound content of up to 8% thereof, a protein containing organic compound content of up to 9% thereof, a protein containing organic compound content of up to 10% thereof, a protein containing organic compound content of up to 11% thereof, a protein containing organic compound content of up to 12% thereof, a protein containing organic compound content of up to 13% thereof, a protein containing organic compound content of up to 14% thereof or a protein containing organic compound content of up to 15% thereof.

The sand content may be less than 5% thereof, less than 4% thereof, less than 3% thereof, less than 2% thereof, less than 1% thereof or less than 0.5% thereof. The mineral content may be less than 5% thereof, less than 4% thereof, less than 3% thereof, less than 2% thereof, less than 1% thereof or less than 0.5% thereof. The dirt content may be less than 5% thereof, less than 4% thereof, less than 3% thereof, less than 2% thereof, less than 1% thereof or less than 0.5% thereof.

The caloric value of the animal feed or animal media 450 may be in the range of 5000-16,000 BTU/Pound. It is noted that the caloric value of the animal feed or animal media 450 may be in the range of 5000-6000 BTU/Pound; in the range of 6000-7000 BTU/Pound; in the range of 7000-8000 BTU/Pound; in the range of 8000-9000 BTU/Pound; in the range of 9000-10000 BTU/Pound; in the range of 10000-11000 BTU/Pound; in the range of 11000-12000 BTU/Pound; in the range of 12000-13000 BTU/Pound; in the range of 13000-14000 BTU/Pound; in the range of 14000-15000 BTU/Pound or in the range of 15000-16000 BTU/Pound.

Examples 9 and 10 describe producing animal feed or animal media 450 from sewage 10 in the system described in reference to FIGS. 1 and 13.

Example 9

Figure 14:
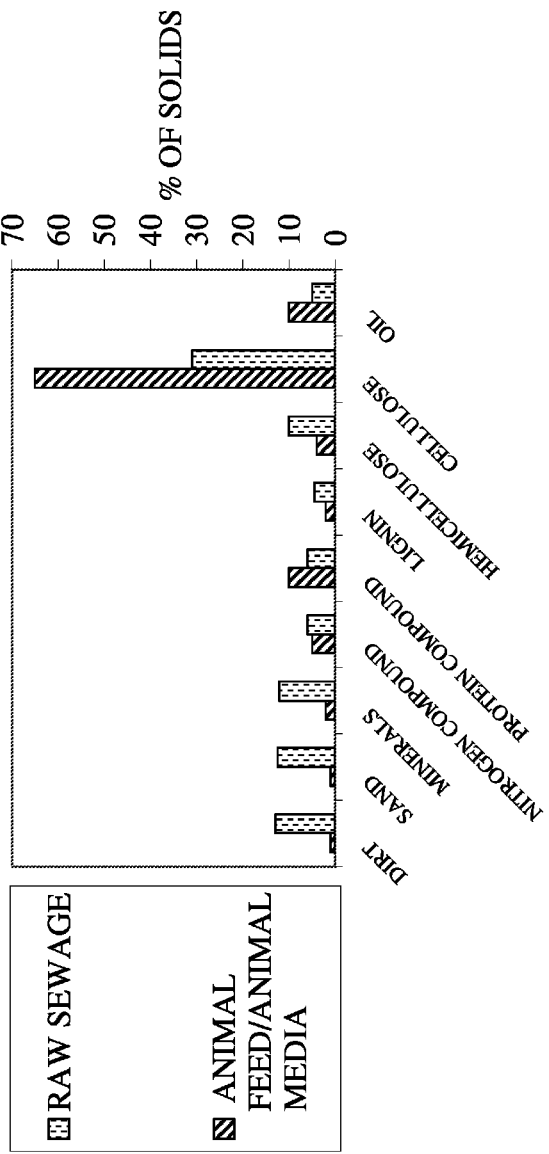
FIG. 14 is a graph of a solid composition obtained from raw sewage Vs. a resulting cellulosic product composition processed in the systems of FIG. 1 and FIG. 13.

Experimental Procedure 100 m$^3$ of raw sewage, including a solid portion of approximately 0.1% of the raw sewage, was obtained from a municipal sewage waste system. As seen in FIG. 14, the composition of the raw sewage solid portion generally comprises 5% oil, 31% cellulose, 10% hemicellulose, 4.5% lignin, 6% protein containing organic compound, 6% nitrogen containing organic compound, 12.1% minerals, 12.5% sand and 12.9% dirt.

The raw sewage was introduced into a hydrocyclone centrifuge at a pressure of 3 Atm for initial sand removal from the raw sewage.

Thereafter the raw sewage was introduced into an entrapping device formed of a net of a 250 micron mesh. Approximately 50 Kg of solids were entrapped within the net. The residual liquid portion was discarded.

Secondary sand removal was performed by sedimentation in a conical-shaped pool wherein the sand sunk to the bottom of the pool. The sedimented sand was discarded.

Dirt removal was performed thereafter in a hydrocyclone centrifuge at a pressure of 3 Atm. The remaining portion was introduced into a magnet containing device wherein a portion of iron was magnetically removed.

The solid portion was introduced into a sterilizer at a temperature of 85° C. for 10 minutes.

Mineral removal was performed by use of a chemical wash wherein the solid portion was boiled at 85° C. for one hour with a solution of distilled water mixed with a 37% hydrochloric acid in a boiling apparatus. The boiled solid portion was thereafter washed 2 times with deionized water.

The solid portion was pressed in a screw press for partial removal of liquids therefrom.

The resultant cellulosic feedstock was thereafter pressed in a disk presser.

The cellulosic feedstock was sterilized in a sterilizer for one hour at a temperature of 100° C.

The resulting portion was partially dried in a drum dryer wherein 80% of the liquids were dried.

The partially dried portion was ground in a ball grinder.

The resultant animal feed or animal media was thereafter packed.

Experimental Results:

As seen in FIG. 14, a resulting animal feed or animal media composition was produced in the system described hereinabove wherein the animal feed or animal media composition generally comprises 10% oil, 65% cellulose, 4% hemicellulose, 2% lignin, 10% protein containing organic compound, 5% nitrogen containing organic compound, 2% minerals, 1% sand and 1% dirt.

Example 10

Figure 15:
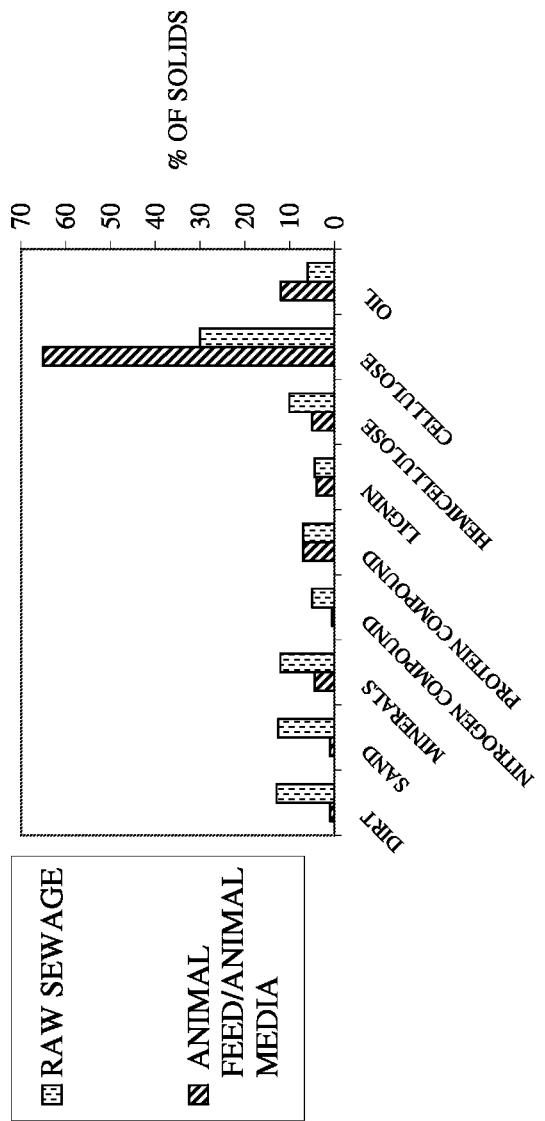
FIG. 15 is a graph of an additional solid composition obtained from raw sewage Vs. a resulting cellulosic product composition processed in the systems of FIG. 1 and FIG. 13.

Experimental Procedure 120 m$^3$ of raw sewage, including a solid portion of approximately 0.05% of the raw sewage, was obtained from a municipal sewage waste system. As seen in FIG. 15, the composition of the raw sewage solid portion generally comprises 6% oil, 30% cellulose, 10% hemicellulose, 4.5% lignin, 7% protein containing organic compound, 5% nitrogen containing organic compound, 12.1% minerals, 12.5% sand and 12.9% dirt.

The raw sewage was introduced into a hydrocyclone centrifuge at a pressure of 3 Atm for initial sand and dirt removal from the raw sewage.

Thereafter the raw sewage was introduced into a vibration separator commercially available from the Sewco company of 8029 US Highway 25 Florence, Ky., USA under catalogue model SS of Sanitary Separators for entrapping solids therein by use of vibration. The residual liquid portion was discarded.

Secondary sand removal was performed by sedimentation in a conical-shaped pool wherein the sand sunk to the bottom of the pool. The sedimented sand was discarded.

The solid portion was pasteurized in a pasteurization device at a temperature of 72° C. for two minutes for partial sterilization thereof.

Mineral removal was performed by use of a chemical wash wherein the solid portion was washed with a solution of distilled water mixed with a 2% hydrochloric acid. The solid portion was thereafter washed with soft water.

The solid portion was pressed in a screw press for partial removal of liquids therefrom.

The resultant cellulosic feedstock was sterilized in a sterilizer for one hour at a temperature of 100° C.

The cellulosic feedstock was partially dried in a greenhouse for 7 days. The cellulosic feedstock was thereafter ground in a ball grinder to 300 microns.

The resultant animal feed or animal media was thereafter packed.

Experimental Results:

As seen in FIG. 15, a resulting animal feed or animal media composition was produced in the system described hereinabove wherein the animal feed or animal media composition generally comprises 12% oil, 65% cellulose, 5% hemicellulose, 4% lignin, 7% protein containing organic compound, 0.5% nitrogen containing organic compound, 4.5% minerals, 1% sand and 1% dirt. The caloric value of the resulting animal feed or animal media is approximately 8500 BTU/Pound.

Figure 16:
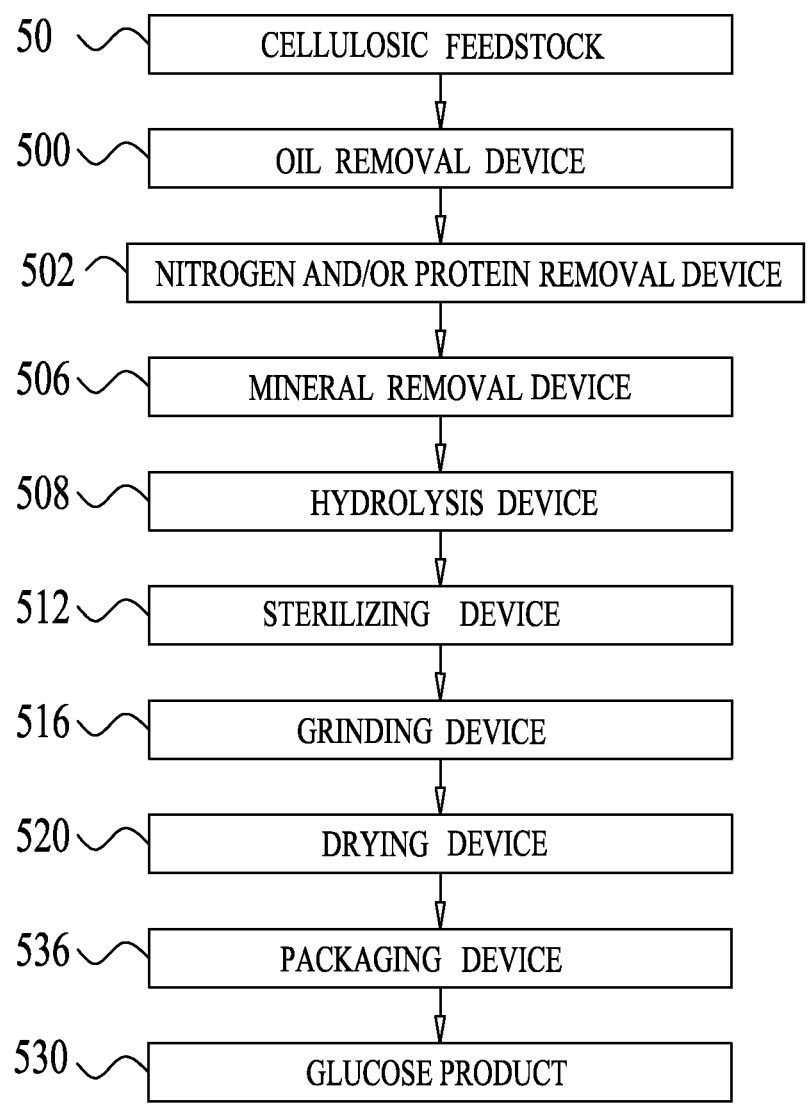
FIG. 16 is a simplified block diagram of a system for manufacturing a cellulosic product from cellulosic feedstock, constructed and operative in accordance with a further embodiment of the present invention.

Reference is now made to FIG. 16, which is a simplified block diagram of a system for manufacturing glucose from cellulosic feedstock, constructed and operative in accordance with an embodiment of the present invention.

As seen in FIG. 16, the cellulosic feedstock 50 may be introduced into an oil removal device 500 for removal of oil therefrom in any suitable manner. Oil removal device 500 may be formed of any one of the abovementioned apparati forming oil removal device 200 of FIG. 7.

The cellulosic feedstock 50 may be introduced into a nitrogen and/or protein removal device 502 for removal of the nitrogen and protein containing compounds by any suitable means. Nitrogen and/or protein removal device 502 may be formed of any one of the abovementioned apparati forming nitrogen and/or protein removal device 104 of FIG. 4.

The cellulosic feedstock 50 may be introduced into a secondary mineral removal device 506 for further removal of minerals within cellulosic feedstock 50 by any suitable means. Secondary mineral removal device 506 may be formed of any one of the abovementioned apparati forming mineral removal device 42 of FIG. 1.

The cellulosic feedstock 50 may be introduced into any suitable hydrolysis device 508 for hydrolyzing cellulosic feedstock 50. Hydrolysis device may employ any suitable means for hydrolyzing the cellulosic feedstock 50, such as by acid hydrolysis; enzymatic hydrolysis or thermochemical hydrolysis.

The cellulosic feedstock 50 may be introduced into a sterilizing device 512 for sterilizing cellulosic feedstock 50 by any suitable means. Sterilizing device 512 may be formed of any one of the abovementioned apparati forming sterilizing device 40 of FIG. 1. Alternatively, the cellulosic feedstock 50 may be partially sterilized, such as by being introduced into a pasteurization device for pasteurizing the cellulosic feedstock 50.

The cellulosic feedstock 50 may be ground in a grinding device 516 by any suitable means. Grinding device 516 may be formed of any one of the above-mentioned apparati forming grinding device 102 of FIG. 4.

The cellulosic feedstock 50 may be introduced into a drying device 520 for at least partial drying of cellulosic feedstock 50 by any suitable means. Drying device 520 may be formed of any one of the abovementioned apparati forming drying device 110 of FIG. 4.

A resulting glucose product 530 may be thereafter packaged in a packaging device 536. Alternatively, the glucose product 530 may further be crystallized or further dried to form glucose 530 of any suitable particle size.

It is appreciated that the order of using the devices described hereinabove may be alternated so as to produce glucose product 530 from cellulosic feedstock 50.

A skilled artisan will appreciate that in the process of producing glucose product 530 some of the devices described hereinabove may be obviated without compromising the quality of the produced glucose product 530.

The resulting glucose product 530 is obtained from the system described hereinabove. The glucose product 530 is a composition substantially comprising an oil content of 1-10% thereof; a cellulose content of 50-99% thereof; a hemicellulose content of 2-45% thereof; a lignin content of less than 12% thereof; a nitrogen containing organic compound content of up to 15% thereof; a protein containing organic compound content of up to 15% thereof; a sand content of less than 5% thereof; a mineral content of less than 5% thereof and a dirt content of less than 5% thereof.

It is noted that the oil content may be an oil content of 1% thereof, an oil content of 1-2% thereof, an oil content of 1-3% thereof, an oil content of 1-4% thereof, an oil content 1-5% thereof, an oil content of 1-6% thereof, an oil content of 1-7% thereof, an oil content of 1-8% thereof, an oil content of 1-9% thereof or an oil content of 10% thereof.

The cellulose content may be a cellulose content of 50-55% thereof, a cellulose content of 55-60% thereof, a cellulose content of 60-65% thereof, a cellulose content of 65-70% thereof, a cellulose content of 70-75% thereof, a cellulose content of 75-80% thereof, a cellulose content of 80-85% thereof, a cellulose content of 85-90% thereof, a cellulose content of 90-95% thereof or a cellulose content of 95-99% thereof.

The hemicellulose content may be a hemicellulose content of 2% thereof, a hemicellulose content of 2-5% thereof, a hemicellulose content of 2-10% thereof, a hemicellulose content of 2-15% thereof; a hemicellulose content of 2-20% thereof, a hemicellulose content of 2-25% thereof, a hemicellulose content of 2-30% thereof, a hemicellulose content of 2-35% thereof, a hemicellulose content of 2-40% thereof or a hemicellulose content of 2-45% thereof.

The lignin content may be a lignin content of less than 12% thereof, a lignin content of less than 11% thereof, a lignin content of less than 10% thereof, a lignin content of less than 9% thereof, a lignin content of less than 8% thereof, a lignin content of less than 7% thereof, a lignin content of less than 6% thereof, a lignin content of less than 5% thereof, a lignin content of less than 4% thereof, a lignin content of less than 3% thereof, a lignin content of less than 2% thereof or a lignin content of less than 1% thereof.

The nitrogen containing organic compound content may be a content of up to 1% thereof, a nitrogen containing organic compound content of up to 2% thereof, a nitrogen containing organic compound content of up to 3% thereof, a nitrogen containing organic compound content of up to 4% thereof, a nitrogen containing organic compound content of up to 5% thereof, a nitrogen containing organic compound content of up to 6% thereof, a nitrogen containing organic compound content of up to 7% thereof, a nitrogen containing organic compound content of up to 8% thereof, a nitrogen containing organic compound content of up to 9% thereof, a nitrogen containing organic compound content of up to 10% thereof, a nitrogen containing organic compound content of up to 11% thereof, a nitrogen containing organic compound content of up to 12% thereof, a nitrogen containing organic compound content of up to 13% thereof, a nitrogen containing organic compound content of up to 14% thereof or a nitrogen containing organic compound content of up to 15% thereof.

The protein containing organic compound content may be a protein containing organic compound content of up to 1% thereof, a protein containing organic compound content of up to 2% thereof, a protein containing organic compound content of up to 3% thereof, a protein containing organic compound content of up to 4% thereof, a protein containing organic compound content of up to 5% thereof, a protein containing organic compound content of up to 6% thereof, a protein containing organic compound content of up to 7% thereof, a protein containing organic compound content of up to 8% thereof, a protein containing organic compound content of up to 9% thereof, a protein containing organic compound content of up to 10% thereof, a protein containing organic compound content of up to 11% thereof, a protein containing organic compound content of up to 12% thereof, a protein containing organic compound content of up to 13% thereof, a protein containing organic compound content of up to 14% thereof or a protein containing organic compound content of up to 15% thereof.

The sand content may be less than 5% thereof, less than 4% thereof, less than 3% thereof, less than 2% thereof, less than 1% thereof or less than 0.5% thereof. The mineral content may be less than 5% thereof, less than 4% thereof, less than 3% thereof, less than 2% thereof, less than 1% thereof or less than 0.5% thereof. The dirt content may be less than 5% thereof, less than 4% thereof, less than 3% thereof, less than 2% thereof, less than 1% thereof or less than 0.5% thereof.

It is noted that the glucose may not be ground to powder but rather remain in a fibrous form. Additionally, any form of a glucose-containing product may be produced in the system described hereinabove. For example, liquid glucose may be produced within the system described hereinabove.

Example 11 describes producing a glucose product 530 from sewage 10 in the system described in reference to FIGS. 1 and 16.

Example 11

Figure 17:
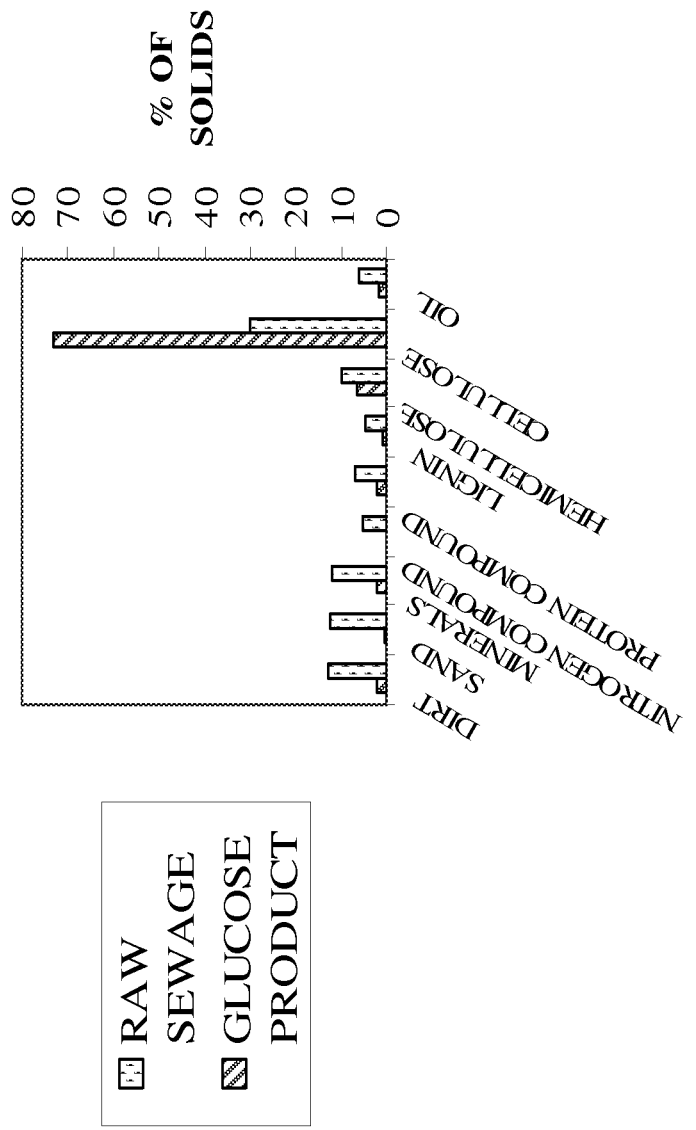
FIG. 17 is a graph of a solid composition obtained from raw sewage Vs. a resulting cellulosic product composition processed in the systems of FIG. 1 and FIG. 16.

Experimental Procedure 100 m³ of raw sewage, including a solid portion of approximately 0.1% of the raw sewage, was obtained from a municipal sewage waste system. As seen in FIG. 17, the composition of the raw sewage solid portion generally comprises 5% oil, 31% cellulose, 10% hemicellulose, 4.5% lignin, 6% protein containing organic compound, 6% nitrogen containing organic compound, 12.1% minerals, 12.5% sand and 12.9% dirt.

The raw sewage was introduced into a hydrocyclone centrifuge at a pressure of 3 Atm for initial sand removal from the raw sewage.

Thereafter the raw sewage was introduced into an entrapping device formed of a net of a 250 micron mesh. Approximately 50 Kg of solids were entrapped within the net. The residual liquid portion was discarded.

Secondary sand removal was performed by sedimentation in a conical-shaped pool wherein the sand sunk to the bottom of the pool. The sedimented sand was discarded.

Dirt removal was performed thereafter in a hydrocyclone centrifuge at a pressure of 3 Atm. The remaining portion was introduced into a magnet containing device wherein a portion of iron was magnetically removed.

The solid portion was introduced into a sterilizer at a temperature of 85° C. for 10 minutes.

Mineral removal was performed by use of a chemical wash wherein the solid portion was boiled at 85° C. for one hour with a solution of distilled water mixed with a 37% hydrochloric acid in a boiling apparatus. The boiled solid portion was thereafter washed 2 times with deionized water.

The solid portion was pressed in a screw press for partial removal of liquids therefrom.

Oil was removed from the resultant cellulosic feedstock by washing the resulting portion with a 1% hexane containing wash. Thereafter the solid portion and hexane containing wash mixture was heated to 80° C. for dissipating the hexane containing wash along with a portion of the oil.

A portion of the nitrogen and protein containing compounds were removed from the cellulosic feedstock by pH Gradient Electrophoresis employing a 10% hydrogen chloride wash.

An enzyme, commercially available from the Genencor Division of Danisco US Inc. of 200 Meridian Centre Blvd. Rochester, N.Y., USA under the name ACCELLERASE® was added to the cellulosic feedstock at a concentration of 5 milliliters per milligram. A buffer of 50 miliMole of sodium acetate with a 5.0 pH was added. The mixture was autoclaved, incubated at 50° C. with shaking at 125 rpm.

The cellulosic feedstock was thereafter ground in a stone grinder.

The solid portion was partially dried in a drum dryer wherein 80% of the liquids were dried.

The partially dried portion was ground in a ball grinder to a powder with a particle length of less than 500 microns.

The powder was thereafter packed.

Experimental Results:

As seen in FIG. 17, a resulting glucose product composition was produced in the system described hereinabove wherein the glucose product composition generally comprises 2% oil, 73.3% cellulose, 6.5% hemicellulose, 2% lignin, 3% protein containing organic compound, 2% nitrogen containing organic compound, 1% minerals, 3% sand and 3% dirt.

Figure 18:
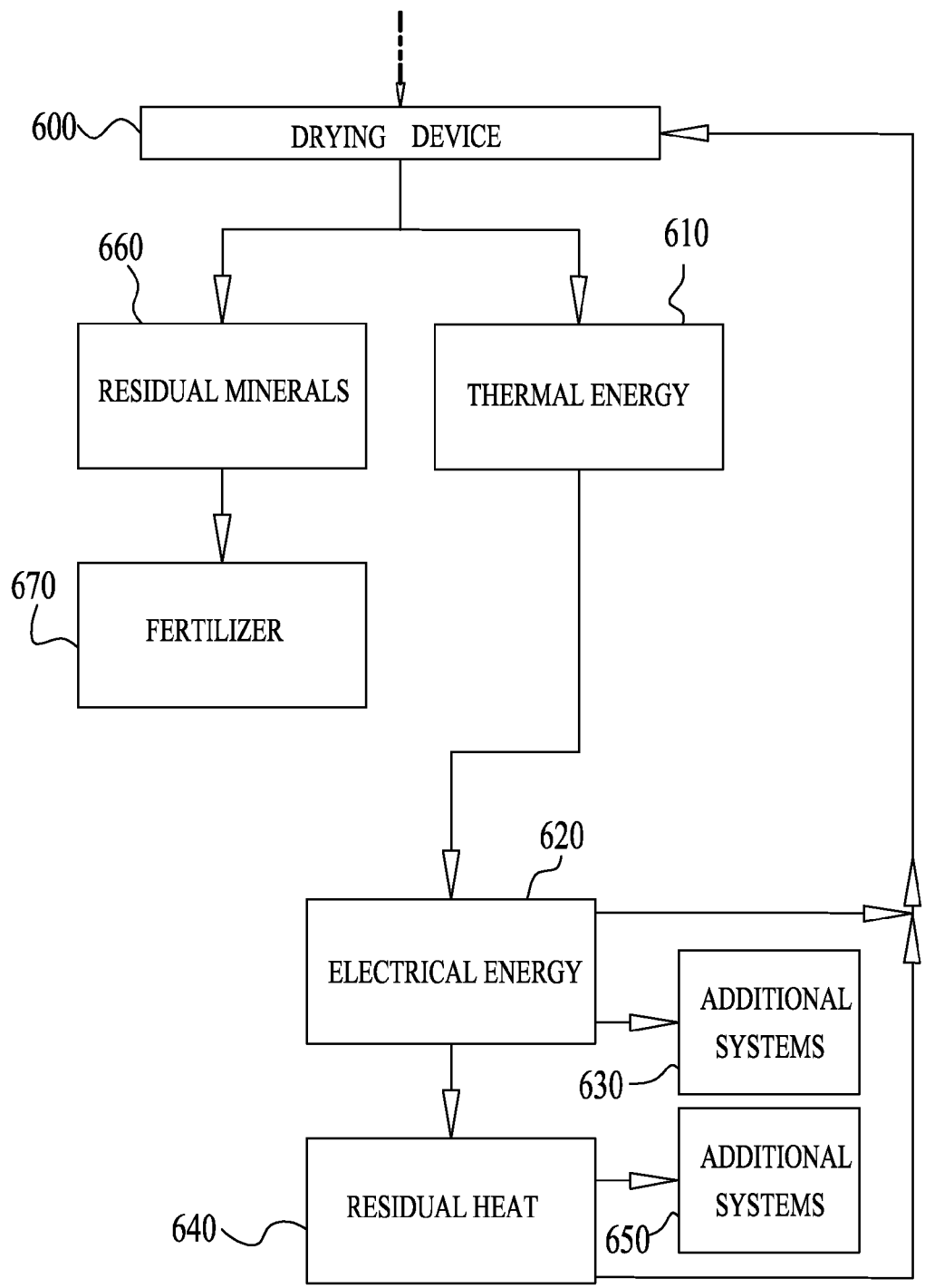
FIG. 18 is a simplified block diagram of a system for utilizing materials and energy exhausted by the systems of FIGS. 1, 4, 7, 10, 13 and/or 16.

Reference is now made to FIG. 18, which is a simplified block diagram of a system for utilizing materials and energy exhausted by the systems of FIGS. 1, 4, 7, 10, 13 and/or 16. As described hereinabove various devices may be employed for manufacturing the cellulosic feedstock and the cellulosic products. It is a particular feature of the present invention that materials and energy exhausted during operation of these devices may be utilized in additional systems or may be fed back to the systems described in reference to FIGS. 1, 4, 7, 10, 13 and/or 16. In FIG. 18 a system for utilizing materials and energy exhausted during operation of a drying device, is illustrated it being appreciated that materials and energy exhausted during operation of other devices may be utilized, mutatis mutandis.

The drying device, here designated by reference numeral 600, may be identical to drying device 110 of FIG. 4, drying device 220 of FIG. 7, drying device 330 of FIG. 10, drying device 410 of FIG. 13 or drying device 520 of FIG. 16. The drying device 600 may employ heat treatment by use of an oven, for example, thereby generating thermal energy 610 by heat exhausted therefrom. The thermal energy 610 may be transformed to electrical energy 620 by any suitable electrical generation means, such as by employing a turbine. The generated electrical energy 620 may be fed back to any of the systems of FIG. 1, 4, 7, 10, 13 or 16, such as to provide electricity for operating the drying device 600 or any other electricity consuming device within the systems of FIG. 1, 4, 7, 10, 13 or 16. Additionally, the electrical energy 620 may be provided to any other additional electricity consuming systems 630.

Residual heat 640, exhausted by the turbine or by any suitable electrical generation means, may be fed back to any of the systems of FIG. 1, 4, 7, 10, 13 or 16, such as to provide heat for operating the drying device 600 or any other heat consuming device within the systems of FIG. 1, 4, 7, 10, 13 or 16. Additionally, the residual heat 640 may be provided to any other additional heat consuming system 650.

During operation of the drying device 600 various materials, such as minerals, typically ash or soot, may be yielded. The residual minerals 660 may be utilized as a fertilizer 670 in any suitable system.

In a non-limiting example the cellulosic feedstock is dried in an oven to yield 1 ton of cellulosic feedstock with a relative humidity of 70-97%. During the drying process 5000-8000 Kilocalories per Kilogram are used thereby generating 5-7 Megawatts of thermal energy. The thermal energy is transformed by a turbine to 1.5-3 Megawatts of electricity. A quantity of 20-150 Kilograms of ash, suitable to be used as a fertilizer, is yielded during the drying process.

Figure 19:
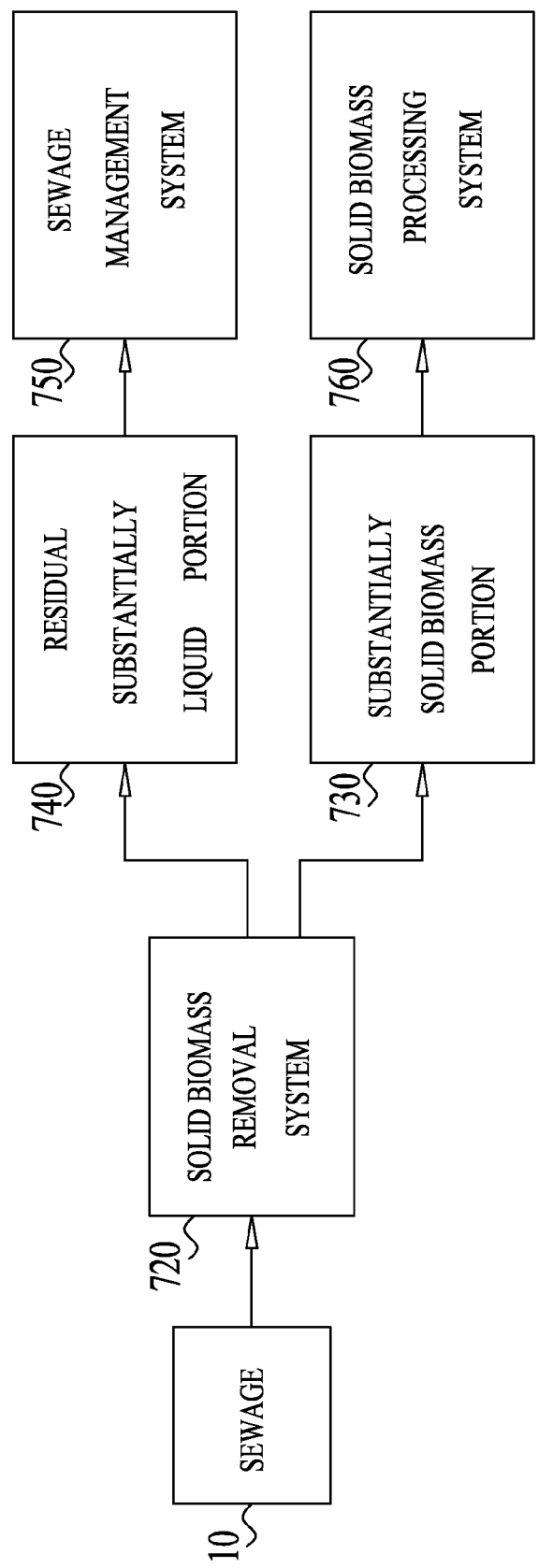
FIG. 19 is a simplified block diagram of a system for gaseous emission reduction from sewage management systems, constructed and operative in accordance with an embodiment of the present invention.

Reference is now made to FIG. 19, which is a simplified block diagram of a system for gaseous emission reduction from sewage management systems, constructed and operative in accordance with an embodiment of the present invention. As seen in FIG. 19, sewage 10 may be introduced into a solid biomass removal system 720.

Sewage 10 may flow into solid biomass removal system 720 via a pipe or by any other suitable means.

Solid biomass removal system 720 is operative to remove solid biomass from sewage 10 by any suitable means. For example, solid biomass may be removed from sewage 10 by a method for removal of a solid portion from sewage disclosed in PCT Publication No. WO 09/023,216 and PCT Publication No. WO 09/142,784, which are hereby incorporated by reference. Additionally, Solid biomass removal system 720 may be similar to solid portion removal device 11 of FIG. 1.

In accordance with an embodiment of the present invention approximately more than 20% of the solid biomass portion of sewage 10 may be removed by the solid biomass removal system 720. In accordance with another embodiment of the present invention a range of approximately 20-30% of the solid biomass portion of sewage 10 may be removed by the solid biomass removal system 720. In accordance with yet another embodiment of the present invention a range of approximately 30-40% of the solid biomass portion of sewage 10 may be removed by the solid biomass removal system 720. In accordance with still another embodiment of the present invention a range of approximately 40-50% of the solid biomass portion of sewage 10 may be removed by the solid biomass removal system 720. In accordance with another embodiment of the present invention a range of approximately 50-60% of the solid biomass portion of sewage 10 may be removed by the solid biomass removal system 720. In accordance with yet another embodiment of the present invention a range of approximately 60-70% of the solid biomass portion of sewage 10 may be removed by the solid biomass removal system 720. In accordance with still another embodiment of the present invention a range of approximately 70-80% of the solid biomass portion of sewage 10 may be removed by the solid biomass removal system 720. In accordance with another embodiment of the present invention a range of approximately 80-90% of the solid biomass portion of sewage 10 may be removed by the solid biomass removal system 720. In accordance with another embodiment of the present invention more than approximately 90% of the solid biomass portion of sewage 10 may be removed by the solid biomass removal system 720.

A substantially solid biomass portion 730 removed from the solid biomass removal system 720 is comprised of solid particles and liquids adsorbed to the solid particles, such as oil and water. The solid biomass portion 730 mainly includes organic matter such as cellulose, though inorganic matter may also adhere thereto.

The solid biomass portion 730 may be similar to entrapped solid particle portion 20 of FIG. 1.

Figure 20:
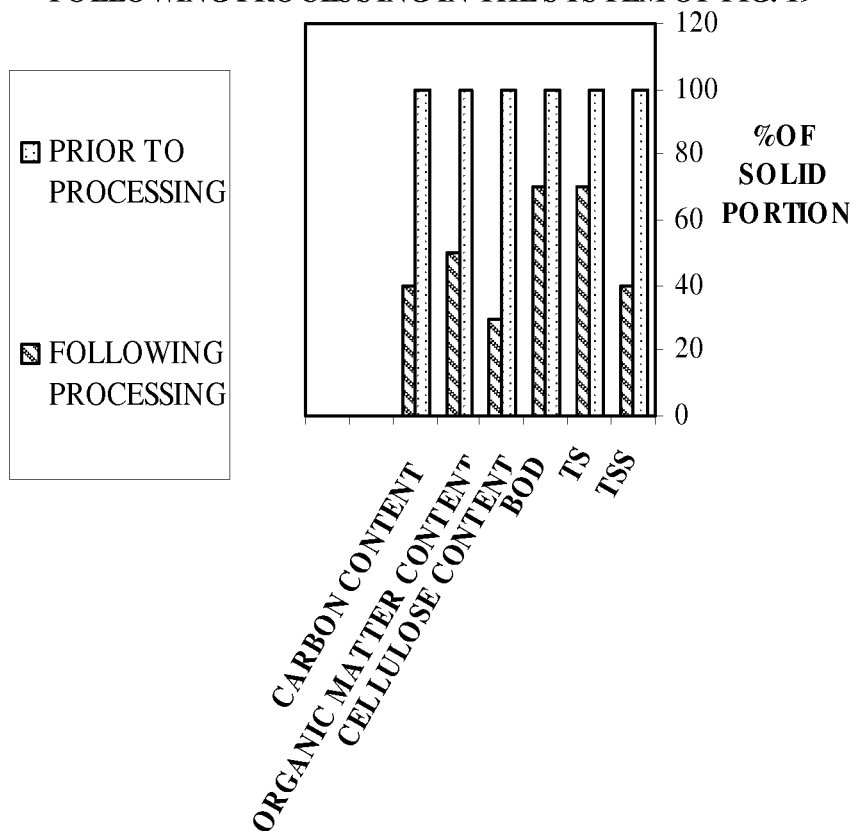
FIG. 20 is a graph of some sewage composition components prior to processing the sewage in the system of FIG. 19 Vs. the resulting composition components following processing in the system of FIG. 19.

A residual substantially liquid portion 740 is discharged from solid biomass removal system 720. Residual portion 740 comprises a smaller amount of solid biomass than sewage 10, following the removal of solid biomass portion 730 by the solid biomass removal system 720. An example showing some sewage composition components prior to removal of the solid biomass and following removal of the solid biomass within solid biomass removal system 720 is shown in FIG. 20 and will be described in detail hereinbelow.

Residual portion 740 may be discarded or may flow to a sewage management system 750, such as back to the municipal sewage waste system, a WWTP or any location prior to digestion within the WWTP, in any suitable manner, such as by conduits. The residual portion 740 may be treated within the sewage management system 750 by any conventional wastewater treatment methods.

The residual portion 740 may be similar to liquid portion 60 of FIG. 1 and sewage management system 750 may be similar to wastewater management system 70 of FIG. 1.

It is well known in the art that gas, such as greenhouse gases, typically carbon dioxide and/or methane, are emitted during conventional treatment within sewage management system 750, typically a WWTP. Sewage management systems 750 that have a sewage stream introduced therein without removal of the solid biomass portion 730 within the solid biomass removal system 720 emit carbon dioxide and/or methane during conventional treatment as follows: (1) the solid biomass portion of sewage 10 is introduced into the sewage management system 750 to be anaerobically aerated and digested into sludge. Greenhouse gases, mainly methane, are emitted during the anaerobic digestion of the solid biomass portion; (2) greenhouse gases, mainly carbon dioxide, are emitted due to conventional electricity consumption caused by operation of the sewage management system 750; and (3) greenhouse gases, mainly methane, are emitted from landfilled sludge.

It is a thus appreciated that removal of solid biomass portion 730 by use of the solid biomass removal system 720 allows for reducing the gaseous emission from sewage management system 750. This is due to the substantially reduced volume of solid biomass entering the sewage management system 750 following removal of solid biomass by biomass removal system 720. Subsequently, gaseous emission during anaerobic processing within the sewage management system 750 is substantially reduced. Additionally, the electrical consumption due to operation of the sewage management system 750 is reduced thus allowing for reduction of gaseous emission therefrom. Moreover, gaseous emission from landfilled sludge is substantially reduced due to the reduced volume of landfilled sludge. It is appreciated that removal of at least 20% of the solid biomass portion results in a reduction of at least 20% of the gaseous emission. Examples 12-16 hereinbelow show that reduced methane and carbon dioxide emission from a conventional WWTP was achieved due to removal of solid biomass by the biomass removal system 720.

The removed solid biomass portion 730 may be introduced into a solid biomass processing system 760, for further processing thereof, as will be described hereinbelow with reference to FIG. 21.

Removal of the solid biomass portion 730 by biomass removal system 720 reduces various components and parameters of the sewage composition, thus allowing reduction of gaseous emission from the sewage composition processed within a sewage management system 750. For example, the carbon content of the sewage 10 may be reduced by approximately 10%-90%; the organic matter content of the sewage 10 may be reduced by approximately 5%-95%; the cellulose content of the sewage 10 may be reduced by approximately 20%-95%; the Biological Oxygen Demand or Biochemical Oxygen Demand (BOD) of the sewage 10 may be reduced by approximately 10%-90%; the Total Solids (TS) of the sewage 10 may be reduced by approximately 5%-90%; and the Total Suspended Solids (TSS) of the sewage 10 may be reduced by approximately 10%-90%.

In accordance with an embodiment of the present invention a range of approximately 10-20% of the carbon content of sewage 10 may be removed by the solid biomass removal system 720. In accordance with another embodiment of the present invention a range of approximately 20-30% of the carbon content of sewage 10 may be removed by the solid biomass removal system 720. In accordance with yet another embodiment of the present invention a range of approximately 30-40% of the carbon content of sewage 10 may be removed by the solid biomass removal system 720. In accordance with still another embodiment of the present invention a range of approximately 40-50% of the carbon content of sewage 10 may be removed by the solid biomass removal system 720. In accordance with another embodiment of the present invention a range of approximately 50-60% of the carbon content of sewage 10 may be removed by the solid biomass removal system 720. In accordance with yet another embodiment of the present invention a range of approximately 60-70% of the carbon content of sewage 10 may be removed by the solid biomass removal system 720. In accordance with still another embodiment of the present invention a range of approximately 70-80% of the carbon content of sewage 10 may be removed by the solid biomass removal system 720. In accordance with another embodiment of the present invention a range of approximately 80-90% of the carbon content of sewage 10 may be removed by the solid biomass removal system 720. In accordance with another embodiment of the present invention more than approximately 90% of the carbon content of sewage 10 may be removed by the solid biomass removal system 720.

In accordance with an embodiment of the present invention approximately more than 5% of the organic matter content of sewage 10 may be removed by the solid biomass removal system 720. In accordance with another embodiment of the present invention a range of approximately 5-20% of the organic matter content of sewage 10 may be removed by the solid biomass removal system 720. In accordance with another embodiment of the present invention a range of approximately 20-30% of the organic matter content of sewage 10 may be removed by the solid biomass removal system 720. In accordance with yet another embodiment of the present invention a range of approximately 30-40% of the organic matter content of sewage 10 may be removed by the solid biomass removal system 720. In accordance with still another embodiment of the present invention a range of approximately 40-50% of the organic matter content of sewage 10 may be removed by the solid biomass removal system 720. In accordance with another embodiment of the present invention a range of approximately 50-60% of the organic matter content of sewage 10 may be removed by the solid biomass removal system 720. In accordance with yet another embodiment of the present invention a range of approximately 60-70% of the organic matter content of sewage 10 may be removed by the solid biomass removal system 720. In accordance with still another embodiment of the present invention a range of approximately 70-80% of the organic matter content of sewage 10 may be removed by the solid biomass removal system 720. In accordance with another embodiment of the present invention a range of approximately 80-90% of the organic matter content of sewage 10 may be removed by the solid biomass removal system 720. In accordance with another embodiment of the present invention approximately 90-95% of the organic matter content of sewage 10 may be removed by the solid biomass removal system 720. In accordance with another embodiment of the present invention more than approximately 95% of the organic matter content of sewage 10 may be removed by the solid biomass removal system 720.

In accordance with an embodiment of the present invention a range of approximately 20-30% of the cellulose content of sewage 10 may be removed by the solid biomass removal system 720. In accordance with yet another embodiment of the present invention a range of approximately 30-40% of the cellulose content of sewage 10 may be removed by the solid biomass removal system 720. In accordance with still another embodiment of the present invention a range of approximately 40-50% of the cellulose content of sewage 10 may be removed by the solid biomass removal system 720. In accordance with another embodiment of the present invention a range of approximately 50-60% of the cellulose content of sewage 10 may be removed by the solid biomass removal system 720. In accordance with yet another embodiment of the present invention a range of approximately 60-70% of the cellulose content of sewage 10 may be removed by the solid biomass removal system 720. In accordance with still another embodiment of the present invention a range of approximately 70-80% of the cellulose content of sewage 10 may be removed by the solid biomass removal system 720. In accordance with another embodiment of the present invention a range of approximately 80-90% of the cellulose content of sewage 10 may be removed by the solid biomass removal system 720. In accordance with another embodiment of the present invention approximately 90-95% of the cellulose content of sewage 10 may be removed by the solid biomass removal system 720. In accordance with another embodiment of the present invention more than approximately 95% of the cellulose content of sewage 10 may be removed by the solid biomass removal system 720.

In accordance with an embodiment of the present invention a range of approximately 10-20% of the BOD of sewage 10 may be removed by the solid biomass removal system 720. In accordance with another embodiment of the present invention a range of approximately 20-30% of the BOD of sewage 10 may be removed by the solid biomass removal system 720. In accordance with yet another embodiment of the present invention a range of approximately 30-40% of the BOD of sewage 10 may be removed by the solid biomass removal system 720. In accordance with still another embodiment of the present invention a range of approximately 40-50% of the BOD of sewage 10 may be removed by the solid biomass removal system 720. In accordance with another embodiment of the present invention a range of approximately 50-60% of the BOD of sewage 10 may be removed by the solid biomass removal system 720. In accordance with yet another embodiment of the present invention a range of approximately 60-70% of the BOD of sewage 10 may be removed by the solid biomass removal system 720. In accordance with still another embodiment of the present invention a range of approximately 70-80% of the BOD of sewage 10 may be removed by the solid biomass removal system 720. In accordance with another embodiment of the present invention a range of approximately 80-90% of the BOD of sewage 10 may be removed by the solid biomass removal system 720. In accordance with another embodiment of the present invention more than approximately 90% of the BOD of sewage 10 may be removed by the solid biomass removal system 720.

It is noted that the BOD is generally defined as a measure of the capacity of water to consume oxygen during the decomposition of organic matter. The BOD is used to quantitate the degree of sewage refuse pollutants, such as solid biomass, within sewage.

In accordance with an embodiment of the present invention a range of approximately 5-20% of the TS of sewage 10 may be removed by the solid biomass removal system 720. In accordance with another embodiment of the present invention a range of approximately 20-30% of the TS of sewage 10 may be removed by the solid biomass removal system 720. In accordance with yet another embodiment of the present invention a range of approximately 30-40% of the TS of sewage 10 may be removed by the solid biomass removal system 720. In accordance with still another embodiment of the present invention a range of approximately 40-50% of the TS of sewage 10 may be removed by the solid biomass removal system 720. In accordance with another embodiment of the present invention a range of approximately 50-60% of the TS of sewage 10 may be removed by the solid biomass removal system 720. In accordance with yet another embodiment of the present invention a range of approximately 60-70% of the TS of sewage 10 may be removed by the solid biomass removal system 720. In accordance with still another embodiment of the present invention a range of approximately 70-80% of the TS of sewage 10 may be removed by the solid biomass removal system 720. In accordance with another embodiment of the present invention a range of approximately 80-90% of the TS of sewage 10 may be removed by the solid biomass removal system 720. In accordance with another embodiment of the present invention more than approximately 90% of the TS of sewage 10 may be removed by the solid biomass removal system 720.

In accordance with an embodiment of the present invention a range of approximately 10-20% of the TSS of sewage 10 may be removed by the solid biomass removal system 720. In accordance with another embodiment of the present invention a range of approximately 20-30% of the TSS of sewage 10 may be removed by the solid biomass removal system 720. In accordance with yet another embodiment of the present invention a range of approximately 30-40% of the TSS of sewage 10 may be removed by the solid biomass removal system 720. In accordance with still another embodiment of the present invention a range of approximately 40-50% of the TSS of sewage 10 may be removed by the solid biomass removal system 720. In accordance with another embodiment of the present invention a range of approximately 50-60% of the TSS of sewage 10 may be removed by the solid biomass removal system 720. In accordance with yet another embodiment of the present invention a range of approximately 60-70% of the TSS of sewage 10 may be removed by the solid biomass removal system 720. In accordance with still another embodiment of the present invention a range of approximately 70-80% of the TSS of sewage 10 may be removed by the solid biomass removal system 720. In accordance with another embodiment of the present invention a range of approximately 80-90% of the TSS of sewage 10 may be removed by the solid biomass removal system 720. In accordance with another embodiment of the present invention more than approximately 90% of the TSS of sewage 10 may be removed by the solid biomass removal system 720.

Reduction of methane and carbon dioxide emission from a conventional WWTP by removal of solid biomass by the biomass removal system 20 is described in Examples 12-16 herein below.

Example 12

Approximately 40% of solid biomass, including cellulose, was removed from sewage prior to entering a relatively large scale WWTP of the municipality of Tel-Aviv, Israel. The solid biomass was removed by a solid biomass removal system comprising a series of nettings with apertures of a few microns.

As seen in FIG. 20, following removal of the solid biomass the carbon content of the sewage was reduced by approximately 60%; the organic matter content of the sewage was reduced by approximately 50%; the cellulose content of the sewage was reduced by approximately 70%; the BOD of the sewage was reduced by approximately 30%; the TS of the sewage was reduced by approximately 30%; and the TSS of the sewage was reduced by approximately 60%. Thus it is seen that the biomass portion of the sewage entering the WWTP was significantly reduced.

Example 13

The gaseous emission reduction was assessed in the relatively large scale WWTP of the municipality of Tel-Aviv, Israel. The assessment was based on the assumption that the WWTP operates in open, anaerobic lagoons, i.e. the digestion of the sewage is performed anaerobically. The reduced gaseous emission is presented in Certified Emission Reduction (CER) units per year. CER is generally defined as a ton of carbon credits, which is an allowance for permitting an emission of a ton of carbon dioxide within a carbon credit system. The carbon credit system was ratified in conjunction with the Kyoto Protocol aiming to reduce global carbon dioxide emissions. Additional gaseous emissions are measured in equivalent CER units. For example, one ton of emitted methane is quantitated as 21 CER units in Examples 13-18, though it is appreciated that the quantification of methane to CER units may vary.

Approximately 40% of solid biomass, including cellulose, was removed from the sewage prior to entering the WWTP. The solid biomass was removed by a solid biomass removal system comprising a series of nettings with apertures of a few microns. The solid biomass portion of the sewage entering the WWTP was significantly reduced. Consequentially the methane emission, which is due to anaerobic processing within the sewage management system, was decreased by approximately 141,000 CER units per year. Additionally, the methane emission due to landfilled sludge, was decreased by approximately CER 10,000 units per year.

Removal of the solid biomass reduced the operational electrical consumption of the WWTP by approximately 18%, thereby reducing the gaseous emission by approximately 13,000 CER units per year.

Figure 22:
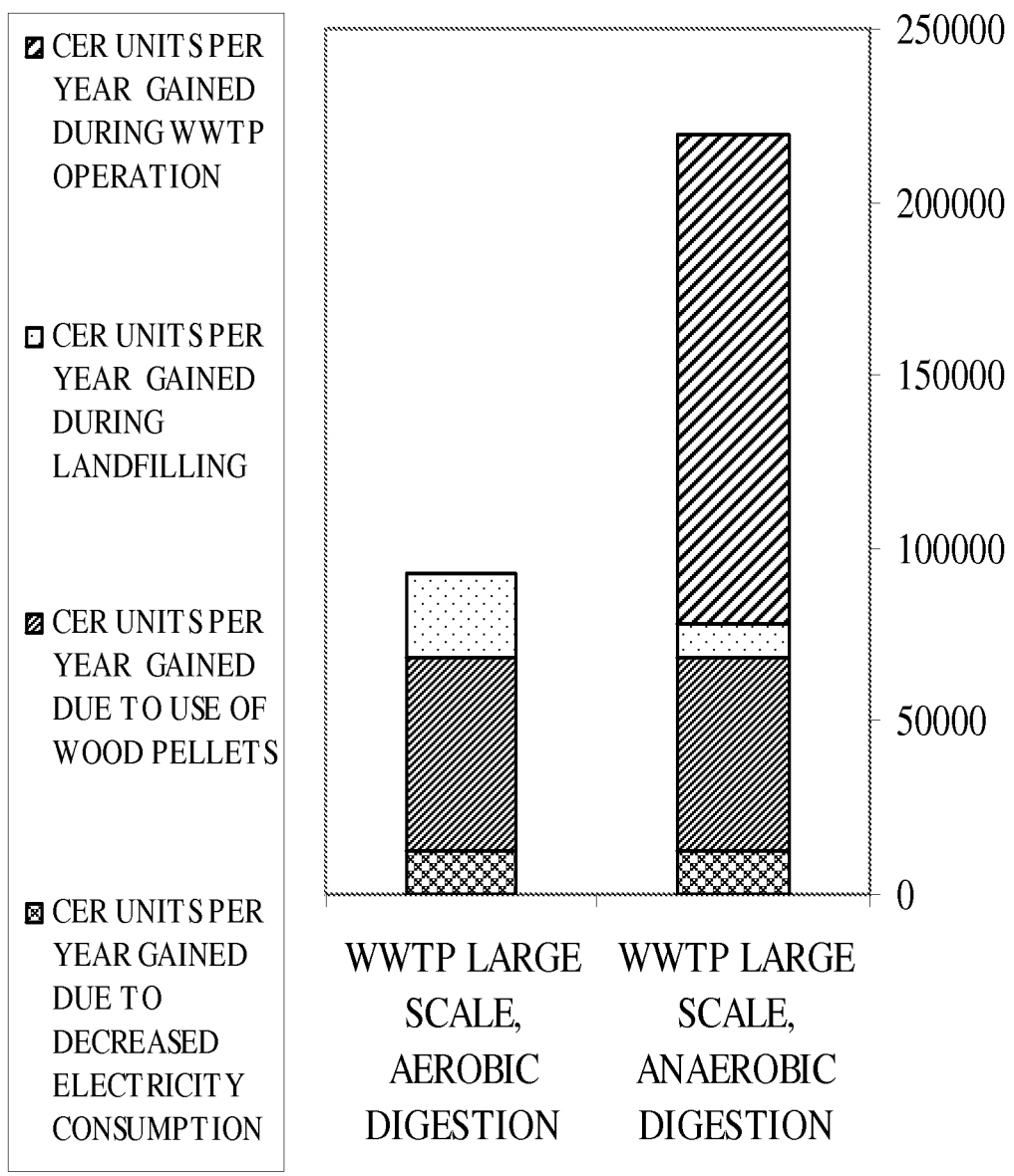
FIG. 22 is a graph of Certified Emission Reduction (CER) units per year gained by use of the systems of FIGS. 19 and 21 in a large scale Wastewater Treatment Plant (WWTP)

A graph showing the CER units per year gained in Example 13 is shown in FIG. 22.

Example 14

The gaseous emission reduction was assessed in a relatively large scale WWTP of the municipality of Tel-Aviv, Israel. The assessment was based on the assumption that the WWTP operates in open, aerobic lagoons, i.e. the digestion of the sewage is performed aerobically. The reduced gaseous emission is presented in CER units per year.

Approximately 40% of solid biomass, including cellulose, was removed from the sewage prior to entering the WWTP. The solid biomass was removed by a solid biomass removal system comprising a series of nettings with apertures of a few microns. Consequentially, methane emission due to landfilled sludge, was decreased by approximately 25,000 CER units per year.

Removal of the solid biomass reduced the operational electrical consumption of the WWTP by approximately 18%, thereby reducing the gaseous emission by approximately 13,000 CER units per year.

It is noted that due to aerobic operation of the WWTP methane is not emitted into the atmosphere during operation of the WWTP.

A graph showing the CER units per year gained in Example 14 is shown in FIG. 22.

Example 15

The gaseous emission reduction was assessed in a relatively small scale WWTP of about a 15% of the size of the municipal Tel Aviv WWTP. The assessment was based on the assumption that the WWTP operates in open, anaerobic lagoons, i.e. the digestion of the sewage is performed anaerobically. Approximately 40% of solid biomass, including cellulose, was removed from the sewage prior to entering the WWTP. The solid biomass was removed by a solid biomass removal system comprising a series of nettings with apertures of a few microns. The solid biomass portion of the sewage entering the WWTP was significantly reduced. Consequentially the methane emission, which is due to anaerobic processing within the sewage management system, was decreased by approximately 21,150 CER units per year. Additionally, the methane emission due to landfilled sludge, was decreased by approximately CER 1,500 units per year.

Removal of the solid biomass reduced the operational electrical consumption of the WWTP by approximately 18%, thereby reducing the gaseous emission by approximately 1,950 CER units per year.

Figure 23:
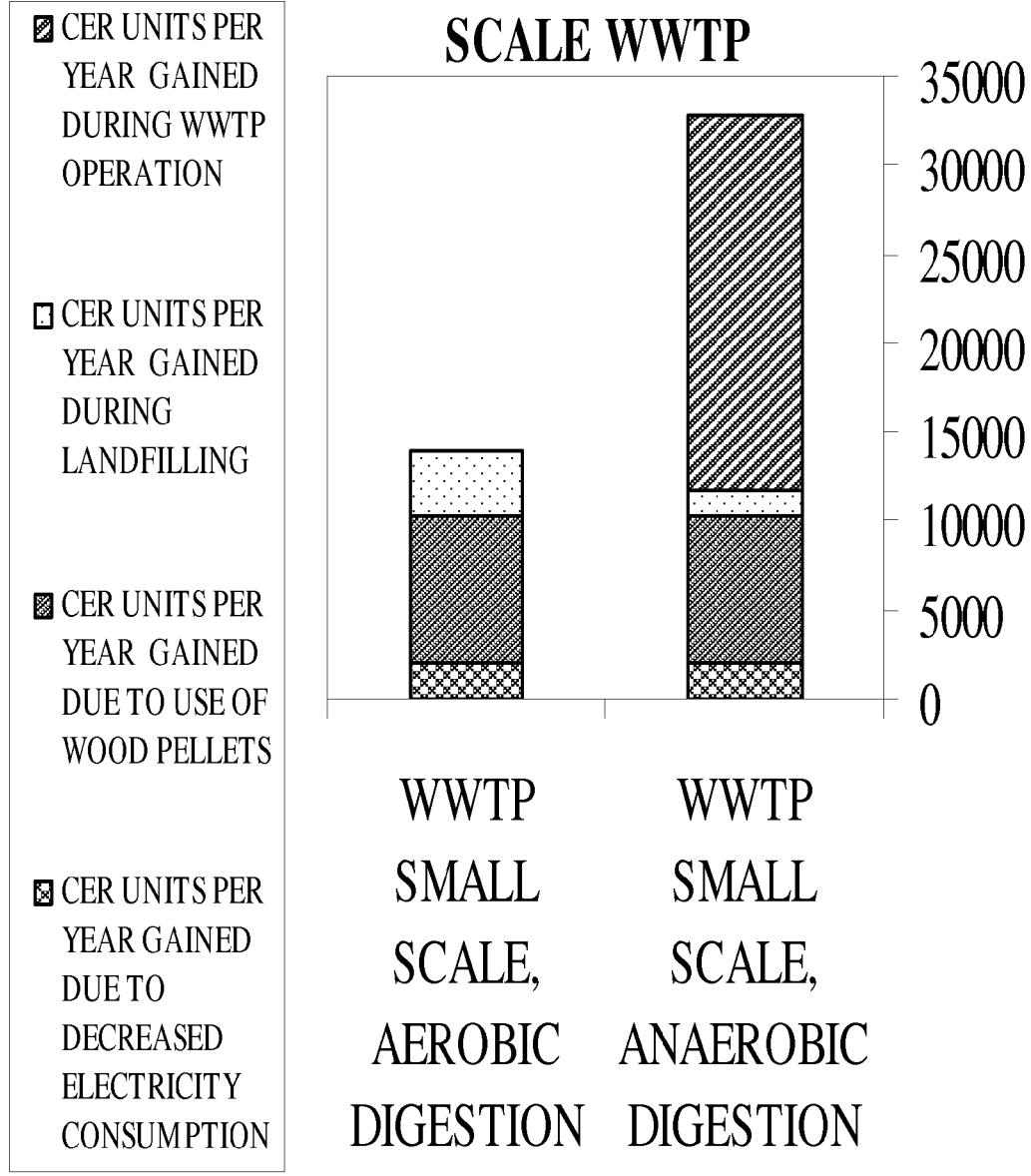
FIG. 23 is a graph of CER units per year gained by use of the systems of FIGS. 19 and 21 in a small scale WWTP.

A graph showing the CER units per year gained in Example 15 is shown in FIG. 23.

Example 16

The gaseous emission reduction was assessed in a relatively small scale WWTP of about a 15% of the size of the municipal Tel Aviv WWTP. The assessment was based on the assumption that the WWTP operates in open, aerobic lagoons, i.e. the digestion of the sewage is performed aerobically. The reduced gaseous emission is presented in CER units per year.

Approximately 40% of solid biomass, including cellulose, was removed from the sewage prior to entering the WWTP. The solid biomass was removed by a solid biomass removal system comprising a series of nettings with apertures of a few microns. Consequentially, methane emission due to landfilled sludge, was decreased by approximately 3,750 CER.

Removal of the solid biomass reduced the operational electrical consumption of the WWTP by approximately 18%, thereby reducing the gaseous emission by approximately 1,950 CER units per year.

A graph showing the CER units per year gained in Example 16 is shown in FIG. 23.

Figure 21:
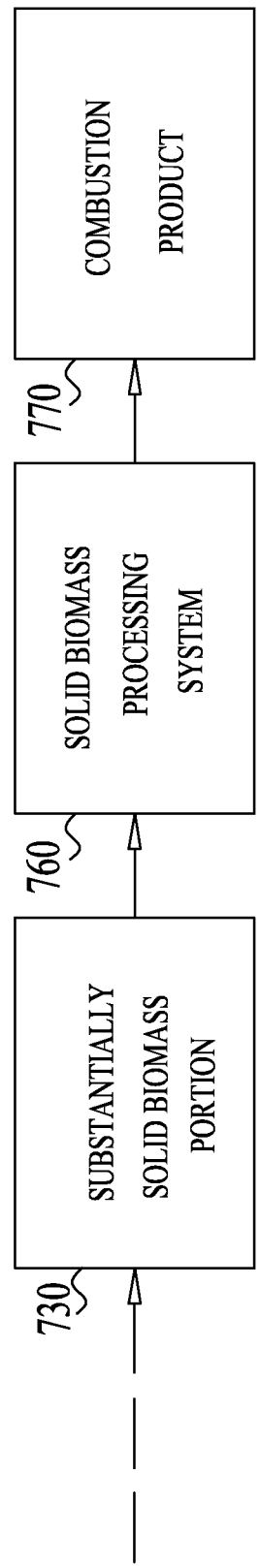
FIG. 21 is a simplified block diagram of a system for reducing gaseous emission caused by combustion of fossil fuels, by utilizing elements of the system of FIG. 19.

Reference is now made to FIG. 21, which is a simplified block diagram of a system for reducing gaseous emission, resulting from combustion of fossil fuels, by utilizing elements of the system of FIG. 19, constructed and operative in accordance with an embodiment of the present invention. As seen in FIG. 21 the removed solid biomass portion 730 of FIG. 19 is introduced into the solid biomass processing system 760, for further processing thereof.

For example, the solid biomass portion 730 within the solid biomass processing system 760 may be sterilized by any suitable means. Additionally, the solid biomass portion 730 may be ground in a grinding device by any suitable means, such as by employment of a screw press, a filter or a blender, a ball grinder, a stone or knife grinder, for example. The solid biomass portion 730 may be ground to any suitable particle size, such as to particles with a length of approximately less than 1 mm, for example.

The solid biomass portion 730 may be introduced into a drying device for partially drying solid biomass portion 730. The drying device may employ any suitable method for partially drying the solid biomass portion 730, such as drying by evaporation employing heat treatment, cryogenic treatment, vacuum, a press, such as a screw press, a drum dryer or a combination thereof.

The solid biomass portion 730 may be thereafter pressed in a pressing device employing any suitable means, such as use of a screw press or a filter press. The solid biomass portion 30 may thereafter be packaged in a packaging device by any suitable means, such as by employing vacuum packing or pellet packing in a pellet machine, for example.

A resulting combustion product 770 is obtained from the system described hereinabove. The combustion product 770 is used for combustion of materials and may be used instead of fossil foil coal. For example, the combustion product 770 may be wood pellets. Thus, utilizing the combustion product 770 allows for reducing gaseous emission resulting from combustion of fossil fuels.

The combustion product 770 may be similar to combustion product 120 of FIG. 4.

It is appreciated that the order of using the devices described hereinabove may be alternated so as to produce combustion product 770 from solid biomass portion 730.

A skilled artisan will appreciate that in the process of producing combustion product 770 some of the devices described hereinabove may be obviated without compromising the quality of the produced combustion product 770. Additionally, the solid biomass portion 730 may be used for combustion without processing thereof within the solid biomass processing system 760.

It is noted that additional products, operative to reduce gaseous emission during combustion, may be produced by processing the solid biomass portion 730 within the solid biomass processing system 760. For example biofuels, such as ethanol may be produced.

Reduction of gaseous emission due to processing the solid biomass portion 730 to produce a combustion product 770 is described in Examples 16 and 17 hereinbelow.

Example 17

Approximately 40% of solid biomass, including cellulose, was removed from the sewage prior to entering the relatively large scale WWTP of the municipality of Tel-Aviv, Israel, described in reference to Examples 12 and 13 hereinabove. The solid biomass was removed by a solid biomass removal system comprising a series of nettings with apertures of a few microns. The removed solid biomass was sterilized and dried in a sterilization oven at 105° C. Thereafter the dried solid biomass was pressed and packaged in a pellet machine. A yield of approximately 22 ton of wooden pellets per year may be thus obtained. The potential heat produced by such a quantity of wooden pellets is approximately 50,544,054 Terajoules. Assuming that combustion efficiency is approximately 90%, the equivalent amount of oil needed to yield 50,544,054 Terajoules is approximately 1787.3 ton per year, thus resulting in a reduction of carbon dioxide emission by approximately 55,000 CER units per year.

A graph showing the CER units per year gained in Example 17 is shown in FIG. 22.

Example 18

Approximately 40% of solid biomass, including cellulose, was removed from the sewage prior to entering a small scale WWTP described in reference to Examples 15 and 16 hereinabove. The solid biomass was removed by a solid biomass removal system comprising a series of nettings with apertures of a few microns. The removed solid biomass was sterilized and dried in a sterilization oven at 105° C. Thereafter the dried solid biomass was pressed and packaged in a pellet machine. A yield of approximately 3.3 ton of wooden pellets per year may be thus obtained. The potential heat produced by such a quantity of wooden pellets is approximately 7,581,608 Terajoules. Assuming that combustion efficiency is approximately 90%, the equivalent amount of oil needed to yield 7,581,608 Terajoules is approximately 268.095 ton per year, thus resulting in a reduction of carbon dioxide emission by approximately 8,250 CER units per year.

A graph showing the CER units per year gained in Example 18 is shown in FIG. 23.

It will be appreciated by persons skilled in the art that the present invention is not limited by what has been particularly shown and described herein above. Rather the scope of the present invention includes both combinations and subcombinations of the various features described hereinabove as well as variations and modifications which would occur to persons skilled in the art upon reading the specifications and which are not in the prior art.

What is claimed:

1. A method for producing a cellulosic feedstock composition from a solid portion of a sewage suspension comprising:
    removing said solid portion from said sewage suspension;
    removing sand from said solid portion;
    removing a mineral from said solid portion; and
    removing dirt from said solid portion,
    wherein the solid portion comprising cellulose is removed from the sewage suspension prior to digestion at a Waste Water Treatment Plant (WWTP),
    thereby producing said cellulosic feedstock composition.

2. A method according to claim 1 wherein said removing sand is operative to decrease a sand content of said composition to less than 5% of said composition.

3. A method according to claim 1 wherein said removing a mineral is operative to decrease a mineral content of said composition to less than 5% of said composition.

4. A method according to claim 1 wherein said removing dirt is operative to decrease a dirt content of said composition to less than 25% of said composition.

5. A method according to claim 1 further comprising at least one of the following:
    at least partially drying said solid portion;
    dewatering said solid portion; and
    sterilizing said solid portion.

6. A method according to claim 1 and wherein said composition comprises:
    an oil content of up to 15% of said composition;
    a cellulose content of 40-99% of said composition;
    a hemicellulose content of 2-20% of said composition;
    a lignin content of less than 15% of said composition;
    a nitrogen containing organic compound content of less than 20% of said composition;
    a protein containing organic compound content of less than 20% of said composition;
    a mineral content of less than 5% of said composition;
    a sand content of less than 5% of said composition; and
    a dirt content of less than 25% of said composition.

7. A method for producing a combustion product composition from a solid portion of a sewage suspension comprising producing said cellulosic feedstock composition according to claim 1 and further comprising at least one of the following:
    grinding said cellulosic feedstock;
    removing a protein containing organic compound from said cellulosic feedstock;
    removing a nitrogen containing organic compound from said cellulosic feedstock;
    pressing said cellulosic feedstock;
    at least partially drying said cellulosic feedstock; and
    adding oil to said cellulosic feedstock,
    thereby producing said combustion product composition.

8. A method for producing a pulp or paper product composition from a solid portion of a sewage suspension comprising producing said cellulosic feedstock composition according to claim 1 and further comprising at least one of the following:
    removing oil from said cellulosic feedstock;
    removing a protein containing organic compound from said cellulosic feedstock;
    removing a nitrogen containing organic compound from said cellulosic feedstock;
    cleaning said cellulosic feedstock;
    delignifying said cellulosic feedstock;
    screening said cellulosic feedstock;
    refining said cellulosic feedstock; and
    at least partially drying said cellulosic feedstock;
    thereby producing said pulp or paper product composition.

9. A method for producing an animal feed or animal media composition from a solid portion of a sewage suspension comprising producing said cellulosic feedstock composition according to claim 1 and further comprising at least one of the following:
    pressing said cellulosic feedstock;
    at least partially sterilizing said cellulosic feedstock;
    at least partially drying said cellulosic feedstock; and
    grinding said cellulosic feedstock,
    thereby producing said animal feed or animal media composition.

10. A method according to claim 5 wherein exhausted thermal energy generated during said drying is transformed to electrical energy.

11. A method according to claim 10 wherein said electrical energy is provided for performing said drying.

12. A method according to claim 11 wherein said drying yields residual minerals and said residual minerals are used as fertilizers.

* * * * *

UNITED STATES PATENT AND TRADEMARK OFFICE
CERTIFICATE OF CORRECTION

| | | |
|---|---|---|
| PATENT NO. | : 8,617,281 B2 | Page 1 of 1 |
| APPLICATION NO. | : 12/700976 | |
| DATED | : December 31, 2013 | |
| INVENTOR(S) | : Aharon et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 588 days.

Signed and Sealed this
Twenty-first Day of July, 2015

Michelle K. Lee
*Director of the United States Patent and Trademark Office*